US008835432B2

(12) United States Patent
Bui et al.

(10) Patent No.: US 8,835,432 B2
(45) Date of Patent: Sep. 16, 2014

(54) HETEROCYCLIC COMPOUNDS AND THEIR USES

(71) Applicant: Amgen Inc., Thousand Oaks, CA (US)

(72) Inventors: Minna Bui, Oakland, CA (US); Timothy David Cushing, Pacifica, CA (US); Felix Gonzalez Lopez De Turiso, San Mateo, CA (US); Xiaolin Hao, Foster City, CA (US); Brian Lucas, San Francisco, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 14/221,499

(22) Filed: Mar. 21, 2014

(65) Prior Publication Data

US 2014/0206694 A1 Jul. 24, 2014

Related U.S. Application Data

(63) Continuation of application No. 13/856,500, filed on Apr. 4, 2013, now Pat. No. 8,716,290.

(60) Provisional application No. 61/620,270, filed on Apr. 4, 2012.

(51) Int. Cl.
| | |
|---|---|
| *C07D 403/12* | (2006.01) |
| *C07D 401/12* | (2006.01) |
| *C07D 401/14* | (2006.01) |
| *A61K 31/506* | (2006.01) |

(52) U.S. Cl.
USPC .......................... 514/248; 514/256; 544/324

(58) Field of Classification Search
USPC .................................................. 514/248, 256
See application file for complete search history.

(56) References Cited

U.S. PATENT DOCUMENTS

| | | | |
|---|---|---|---|
| 7,879,853 B2 * | 2/2011 | Stadlwieser et al. | 514/235.8 |
| 8,716,290 B2 * | 5/2014 | Bui et al. | 514/248 |
| 2010/0331306 A1 * | 12/2010 | Bui et al. | 514/210.21 |

* cited by examiner

*Primary Examiner* — Kahsay Habte
(74) *Attorney, Agent, or Firm* — Richard V. Person

(57) ABSTRACT

Substituted bicyclic heteroaryls and compositions containing them, for the treatment of general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, including but not restricted to autoimmune diseases such as systemic lupus erythematosis (SLE), myestenia gravis, rheumatoid arthritis, acute disseminated encephalomyelitis, idiopathic thrombocytopenic purpura, multiples sclerosis, Sjoegren's syndrome and autoimmune hemolytic anemia, allergic conditions including all forms of hypersensitivity, The present invention also enables methods for treating cancers that are mediated, dependent on or associated with p110δ activity, including but not restricted to leukemias, such as Acute Myeloid leukaemia (AML) Myelo-dysplastic syndrome (MDS) myelo-proliferative diseases (MPD) Chronic Myeloid Leukemia (CML) T-cell Acute Lymphoblastic leukaemia (T-ALL) B-cell Acute Lymphoblastic leukaemia (B-ALL) Non Hodgkins Lymphoma (NHL) B-cell lymphoma and solid tumors, such as breast cancer.

8 Claims, No Drawings

HETEROCYCLIC COMPOUNDS AND THEIR USES

This application is a continuation of, and claims priority to, U.S. patent application Ser. No. 13/856,500, filed on Apr. 4, 2013, which claims the benefit of, and priority to, U.S. Provisional Application No. 61/620,270, filed on Apr. 4, 2012, both of which are hereby incorporated by reference in their entireties and for all purposes as if fully set forth herein.

The present invention relates generally to phosphatidylinositol 3-kinase (PI3K) enzymes, and more particularly to selective inhibitors of PI3K activity and to methods of using such materials.

BACKGROUND OF THE INVENTION

Cell signaling via 3'-phosphorylated phosphoinositides has been implicated in a variety of cellular processes, e.g., malignant transformation, growth factor signaling, inflammation, and immunity (see Rameh et al., J. Biol Chem, 274: 8347-8350 (1999) for a review). The enzyme responsible for generating these phosphorylated signaling products, phosphatidylinositol 3-kinase (PI 3-kinase; PI3K), was originally identified as an activity associated with viral oncoproteins and growth factor receptor tyrosine kinases that phosphorylates phosphatidylinositol (PI) and its phosphorylated derivatives at the 3'-hydroxyl of the inositol ring (Panayotou et al., Trends Cell Biol 2:358-60 (1992)).

The levels of phosphatidylinositol-3,4,5-triphosphate (PIP3), the primary product of PI 3-kinase activation, increase upon treatment of cells with a variety of stimuli. This includes signaling through receptors for the majority of growth factors and many inflammatory stimuli, hormones, neurotransmitters and antigens, and thus the activation of PI3Ks represents one, if not the most prevalent, signal transduction events associated with mammalian cell surface receptor activation (Cantley, Science 296:1655-1657 (2002); Vanhaesebroeck et al. Annu. Rev. Biochem, 70: 535-602 (2001)). PI 3-kinase activation, therefore, is involved in a wide range of cellular responses including cell growth, migration, differentiation, and apoptosis (Parker et al., Current Biology, 5:577-99 (1995); Yao et al., Science, 267:2003-05 (1995)). Though the downstream targets of phosphorylated lipids generated following PI 3-kinase activation have not been fully characterized, it is known that pleckstrin-homology (PH) domain- and FYVE-finger domain-containing proteins are activated when binding to various phosphatidylinositol lipids (Sternmark et al., J Cell Sci, 112:4175-83 (1999); .Lemmon et al., Trends Cell Biol, 7:237-42 (1997)). Two groups of PH-domain containing PI3K effectors have been studied in the context of immune cell signaling, members of the tyrosine kinase TEC family and the serine/threonine kinases of to AGC family. Members of the Tec family containing PH domains with apparent selectivity for PtdIns (3,4,5)$P_3$ include Tec, Btk, Itk and Etk. Binding of PH to $PIP_3$ is critical for tyrsosine kinase activity of the Tec family members (Schaeffer and Schwartzberg, Curr. Opin. Immunol. 12: 282-288 (2000)) AGC family members that are regulated by PI3K include the phosphoinositide-dependent kinase (PDK1), AKT (also termed PKB) and certain isoforms of protein kinase C (PKC) and S6 kinase. There are three isoforms of AKT and activation of AKT is strongly associated with PI3K-dependent proliferation and survival signals. Activation of AKT depends on phosphorylation by PDK1, which also has a 3-phosphoinositide-selective PH domain to recruit it to the membrane where it interacts with AKT. Other important PDK1 substrates are PKC and S6 kinase (Deane and Fruman, Annu. Rev. Immunol. 22_563-598 (2004)). In vitro, some isoforms of protein kinase C(PKC) are directly activated by PIP3. (Buggering et al., Nature, 376:599-602 (1995)).

Presently, the PI 3-kinase enzyme family has been divided into three classes based on their substrate specificities. Class I PI3Ks can phosphorylate phosphatidylinositol (PI), phosphatidylinositol-4-phosphate, and phosphatidyl-inositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidyl-inositol-4-phosphate, whereas Class III PI3Ks can only phosphorylate PI.

The initial purification and molecular cloning of PI 3-kinase revealed that it was a heterodimer consisting of p85 and p110 subunits (Otsu et al., Cell, 65:91-104 (1991); Hiles et al., Cell, 70:419-29 (1992)). Since then, four distinct Class I PI3Ks have been identified, designated PI3K α, β, δ, and γ, each consisting of a distinct 110 kDa catalytic subunit and a regulatory subunit. More specifically, three of the catalytic subunits, i.e., p110α, p110β and p110δ, each interact with the same regulatory subunit, p85; whereas p110γ interacts with a distinct regulatory subunit, p101. As described below, the patterns of expression of each of these PI3Ks in human cells and tissues are also distinct. Though a wealth of information has been accumulated in recent past on the cellular functions of PI 3-kinases in general, the roles played by the individual isoforms are not fully understood.

Cloning of bovine p110α has been described. This protein was identified as related to the *Saccharomyces cerevisiae* protein: Vps34p, a protein involved in vacuolar protein processing. The recombinant p110α product was also shown to associate with p85α, to yield a PI3K activity in transfected COS-1 cells. See Hiles et al., Cell, 70, 419-29 (1992).

The cloning of a second human p110 isoform, designated p110β, is described in Hu et al., Mol Cell Biol, 13:7677-88 (1993). This isoform is said to associate with p85 in cells, and to be ubiquitously expressed, as p110β mRNA has been found in numerous human and mouse tissues as well as in human umbilical vein endothelial cells, Jurkat human leukemic T cells, 293 human embryonic kidney cells, mouse 3T3 fibroblasts, HeLa cells, and NBT2 rat bladder carcinoma cells. Such wide expression suggests that this isoform is broadly important in signaling pathways.

Identification of the p110δ isoform of PI 3-kinase is described in Chantry et al., J Biol Chem, 272:19236-41 (1997). It was observed that the human p110δ isoform is expressed in a tissue-restricted fashion. It is expressed at high levels in lymphocytes and lymphoid tissues and has been shown to play a key role in PI 3-kinase-mediated signaling in the immune system (Al-Alwan et. al. JI 178: 2328-2335 (2007); Okkenhaug et al JI, 177: 5122-5128 (2006); Lee et al. PNAS, 103: 1289-1294 (2006)). P110δ has also been shown to be expressed at lower levels in breast cells, melanocytes and endothelial cells (Vogt et al. Virology, 344: 131-138 (2006) and has since been implicated in conferring selective migratory properties to breast cancer cells (Sawyer et al. Cancer Res. 63:1667-1675 (2003)). Details concerning the P110δ isoform also can be found in U.S. Pat. Nos. 5,858,753; 5,822,910; and 5,985,589. See also, Vanhaesebroeck et al., Proc Nat. Acad Sci USA, 94:4330-5 (1997), and international publication WO 97/46688.

In each of the PI3Kα, β, and δ subtypes, the p85 subunit acts to localize PI 3-kinase to the plasma membrane by the interaction of its SH2 domain with phosphorylated tyrosine residues (present in an appropriate sequence context) in target proteins (Rameh et al., Cell, 83:821-30 (1995)). Five isoforms of p85 have been identified (p85α, p85β, p55γ, p55α and p50α) encoded by three genes. Alternative transcripts of Pik3r1 gene encode the p85 α, p55 α and p50α proteins (Deane and Fruman, Annu. Rev. Immunol. 22: 563-598 (2004)). p85α is ubiquitously expressed while p85β, is primarily found in the brain and lymphoid tissues (Volinia et al., Oncogene, 7:789-93 (1992)). Association of the p85 subunit to the PI 3-kinase p110α, β, or δ catalytic subunits appears to be required for the catalytic activity and stability of these enzymes. In addition, the binding of Ras proteins also upregulates PI 3-kinase activity.

The cloning of p110γ revealed still further complexity within the PI3K family of enzymes (Stoyanov et al., Science, 269:690-93 (1995)). The p110γ isoform is closely related to p110α and p110β (45-48% identity in the catalytic domain), but as noted does not make use of p85 as a targeting subunit. Instead, p110γ binds a p101 regulatory subunit that also binds to the βγ subunits of heterotrimeric G proteins. The p101 regulatory subunit for PI3 Kgamma was originally cloned in swine, and the human ortholog identified subsequently (Krugmann et al., J Biol Chem, 274:17152-8 (1999)). Interaction between the N-terminal region of p101 with the N-terminal region of p110γ is known to activate PI3Kγ through Gβγ. Recently, a p101-homologue has been identified, p84 or p87$^{PIKAP}$ (PI3Kγ adapter protein of 87 kDa) that binds p110γ (Voigt et al. JBC, 281: 9977-9986 (2006), Suire et al. Curr. Biol. 15: 566-570 (2005)). p87$^{PIKAP}$ is homologous to p101 in areas that bind p110γ and Gβγ and also mediates activation of p110γ downstream of G-protein-coupled receptors. Unlike p101, p87$^{PIKAP}$ is highly expressed in the heart and may be crucial to PI3Kγ cardiac function.

A constitutively active PI3K polypeptide is described in international publication WO 96/25488. This publication discloses preparation of a chimeric fusion protein in which a 102-residue fragment of p85 known as the inter-SH2 (iSH2) region is fused through a linker region to the N-terminus of murine p110. The p85 iSH2 domain apparently is able to activate PI3K activity in a manner comparable to intact p85 (Klippel et al., Mol Cell Biol, 14:2675-85 (1994)).

Thus, PI 3-kinases can be defined by their amino acid identity or by their activity. Additional members of this growing gene family include more distantly related lipid and protein kinases including Vps34 TOR1, and TOR2 of Saccharomyces cerevisiae (and their mammalian homologs such as FRAP and mTOR), the ataxia telangiectasia gene product (ATR) and the catalytic subunit of DNA-dependent protein kinase (DNA-PK). See generally, Hunter, Cell, 83:1-4 (1995).

PI 3-kinase is also involved in a number of aspects of leukocyte activation. A p85-associated PI 3-kinase activity has been shown to physically associate with the cytoplasmic domain of CD28, which is an important costimulatory molecule for the activation of T-cells in response to antigen (Pages et al., Nature, 369:327-29 (1994); Rudd, Immunity, 4:527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al., Science, 251:313-16 (1991)). Mutation of CD28 such that it can no longer interact with PI 3-kinase leads to a failure to initiate IL2 production, suggesting a critical role for PI 3-kinase in T cell activation.

Specific inhibitors against individual members of a family of enzymes provide invaluable tools for deciphering functions of each enzyme. Two compounds, LY294002 and wortmannin, have been widely used as PI 3-kinase inhibitors. These compounds, however, are nonspecific PI3K inhibitors, as they do not distinguish among the four members of Class I PI 3-kinases. For example, the IC$_{50}$ values of wortmannin against each of the various Class I PI 3-kinases are in the range of 1-10 nM. Similarly, the IC$_{50}$ values for LY294002 against each of these PI 3-kinases is about 1 μM (Fruman et al., Ann Rev Biochem, 67:481-507 (1998)). Hence, the utility of these compounds in studying the roles of individual Class I PI 3-kinases is limited.

Based on studies using wortmannin, there is evidence that PI 3-kinase function also is required for some aspects of leukocyte signaling through G-protein coupled receptors (Thelen et al., Proc Natl Acad Sci USA, 91:4960-64 (1994)). Moreover, it has been shown that wortmannin and LY294002 block neutrophil migration and superoxide release. However, inasmuch as these compounds do not distinguish among the various isoforms of PI3K, it remains unclear from these studies which particular PI3K isoform or isoforms are involved in these phenomena and what functions the different Class I PI3K enzymes perform in both normal and diseased tissues in general. The co-expression of several PI3K isoforms in most tissues has confounded efforts to segregate the activities of each enzyme until recently.

The separation of the activities of the various PI3K isozymes has been advanced recently with the development of genetically manipulated mice that allowed the study of isoform-specific knock-out and kinase dead knock-in mice and the development of more selective inhibitors for some of the different isoforms. P110α and p110β knockout mice have been generated and are both embryonic lethal and little information can be obtained from these mice regarding the expression and function of p110 alpha and beta (Bi et al. Mamm. Genome, 13:169-172 (2002); Bi et al. J. Biol. Chem. 274: 10963-10968 (1999)). More recently, p110α kinase dead knock in mice were generated with a single point mutation in the DFG motif of the ATP binding pocket (p110αD$^{933A}$) that impairs kinase activity but preserves mutant p110α kinase expression. In contrast to knock out mice, the knockin approach preserves signaling complex stoichiometry, scaffold functions and mimics small molecule approaches more realistically than knock out mice. Similar to the p110α KO mice, p110αD$^{933A}$ homozygous mice are embryonic lethal. However, heterozygous mice are viable and fertile but display severely blunted signaling via insulin-receptor substrate (IRS) proteins, key mediators of insulin, insulin-like growth factor-1 and leptin action. Defective responsiveness to these hormones leads to hyperinsulinaemia, glucose intolerance, hyperphagia, increase adiposity and reduced overall growth in heterozygotes (Foukas, et al. Nature, 441: 366-370 (2006)). These studies revealed a defined, non-redundant role for p110α as an intermediate in IGF-1, insulin and leptin signaling that is not substituted for by other isoforms. We will have to await the description of the p110β kinase-dead knock in mice to further understand the function of this isoform (mice have been made but not yet published; Vanhaesebroeck).

P110γ knock out and kinase-dead knock in mice have both been generated and overall show similar and mild phenotypes with primary defects in migration of cells of the innate immune system and a defect in thymic development of T cells (Li et al. Science, 287: 1046-1049 (2000), Sasaki et al. Science, 287: 1040-1046 (2000), Patrucco et al. Cell, 118: 375-387 (2004)).

Similar to p110γ, PI3K delta knock out and kinase-dead knock-in mice have been made and are viable with mild and like phenotypes. The p110δ$^{D910A}$ mutant knock in mice demonstrated an important role for delta in B cell development and function, with marginal zone B cells and CDS+ B1 cells nearly undetectable, and B- and T cell antigen receptor signaling (Clayton et al. J. Exp. Med. 196:753-763 (2002); Okkenhaug et al. Science, 297: 1031-1034 (2002)). The p110δ$^{D910A}$ mice have been studied extensively and have elucidated the diverse role that delta plays in the immune system. T cell dependent and T cell independent immune responses are severely attenuated in p110δ$^{D910A}$ and secretion of TH1 (INF-γ) and TH2 cytokine (IL-4, IL-5) are impaired (Okkenhaug et al. J. Immunol. 177: 5122-5128 (2006)). A human patient with a mutation in p110δ has also recently been described. A taiwanese boy with a primary B cell immunodeficiency and a gamma-hypoglobulinemia of previously unkown aetiology presented with a single base-pair substitution, m.3256G to A in codon 1021 in exon 24 of p110δ. This mutation resulted in a mis-sense amino acid substitution (E to K) at codon 1021, which is located in the highly conserved catalytic domain of p110δ protein. The patient has no other identified mutations his phenotype is consistent with p110δ deficiency in mice as far as studied. (Jou et al. Int. J. Immunogenet. 33: 361-369 (2006)).

Isoform-selective small molecule compounds have been developed with varying success to all Class I PI3 kinase isoforms (Ito et al. J. Pharm. Exp. Therapeut., 321:1-8 (2007)) Inhibitors to alpha are desirable because mutations in p110α have been identified in several solid tumors; for example, an amplification mutation of alpha is associated with 50% of ovarian, cervical, lung and breast cancer and an activation mutation has been described in more than 50% of bowel and 25% of breast cancers (Hennessy et al. Nature Reviews, 4: 988-1004 (2005)). Yamanouchi has developed a compound YM-024 that inhibits alpha and delta equi-potently and is 8- and 28-fold selective over beta and gamma respectively (Ito et al. J. Pharm. Exp. Therapeut., 321:1-8 (2007)).

P110β is involved in thrombus formation (Jackson et al. Nature Med. 11: 507-514 (2005)) and small molecule inhibitors specific for this isoform are thought after for indication involving clotting disorders (TGX-221: 0.007 uM on beta; 14-fold selective over delta, and more than 500-fold selective over gamma and alpha) (Ito et al. J. Pharm. Exp. Therapeut., 321:1-8 (2007)).

Selective compounds to p110γ are being developed by several groups as immunosuppressive agents for autoimmune disease (Rueckle et al. Nature Reviews, 5: 903-918 (2006)). Of note, AS 605240 has been shown to be efficacious in a mouse model of rheumatoid arthritis (Camps et al. Nature Medicine, 11: 936-943 (2005)) and to delay onset of disease in a model of systemic lupus erythematosis (Barber et al. Nature Medicine, 11: 933-935 (205)).

Delta-selective inhibitors have also been described recently. The most selective compounds include the quinazolinone purine inhibitors (PIK39 and IC87114). IC87114 inhibits p110δ in the high nanomolar range (triple digit) and has greater than 100-fold selectivity against p110α, is 52 fold selective against p110β but lacks selectivity against p110γ (approx. 8-fold). It shows no activity against any protein kinases tested (Knight et al. Cell, 125: 733-747 (2006)). Using delta-selective compounds or genetically manipulated mice (p110δ$^{D910A}$) it was shown that in addition to playing a key role in B and T cell activation, delta is also partially involved in neutrophil migration and primed neutrophil respiratory burst and leads to a partial block of antigen-IgE mediated mast cell degranulation (Condliffe et al. Blood, 106: 1432-1440 (2005); Ali et al. Nature, 431: 1007-1011 (2002)). Hence p110δ is emerging as an important mediator of many key inflammatory responses that are also known to participate in aberrant inflammatory conditions, including but not limited to autoimmune disease and allergy. To support this notion, there is a growing body of p110δ target validation data derived from studies using both genetic tools and pharmacologic agents. Thus, using the delta-selective compound IC 87114 and the p110δ$^{D910A}$ mice, Ali et al. (Nature, 431: 1007-1011 (2002)) have demonstrated that delta plays a critical role in a murine model of allergic disease. In the absence of functional delta, passive cutaneous anaphylaxis (PCA) is significantly reduced and can be attributed to a reduction in allergen-IgE induced mast cell activation and degranulation. In addition, inhibition of delta with IC 87114 has been shown to significantly ameliorate inflammation and disease in a murine model of asthma using ovalbumin-induced airway inflammation (Lee et al. FASEB, 20: 455-465 (2006). These data utilizing compound were corroborated in p110δ$^{D910A}$ mutant mice using the same model of allergic airway inflammation by a different group (Nashed et al. Eur. J. Immunol. 37:416-424 (2007)).

There exists a need for further characterization of PI3Kδ function in inflammatory and auto-immune settings. Furthermore, our understanding of PI3Kδ requires further elaboration of the structural interactions of p110δ, both with its regulatory subunit and with other proteins in the cell. There also remains a need for more potent and selective or specific inhibitors of PI3K delta, in order to avoid potential toxicology associated with activity on isozymes p110 alpha (insulin signaling) and beta (platelet activation). In particular, selective or specific inhibitors of PI3Kδ are desirable for exploring the role of this isozyme further and for development of superior pharmaceuticals to modulate the activity of the isozyme.

SUMMARY

The present invention comprises a new compounds having improved properties and biological activity in human PI3Kδ

DETAILED DESCRIPTION

One aspect of the invention relates to compounds having the structures

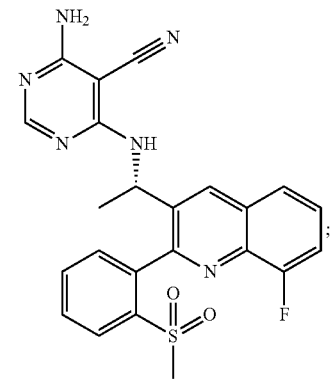 [SMILES: C[C@H](Nc1ncnc(N)c1C#N)c1cc2cccc(F)c2nc1-c1ccccc1S(C)(=O)=O]

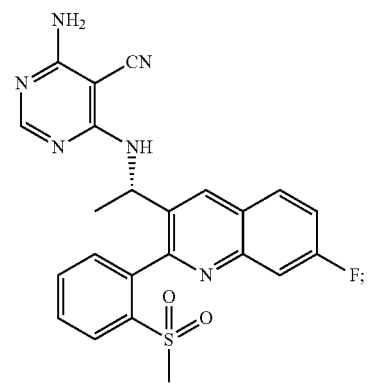 [SMILES: C[C@H](Nc1ncnc(N)c1C#N)c1cc2ccc(F)cc2nc1-c1ccccc1S(C)(=O)=O]

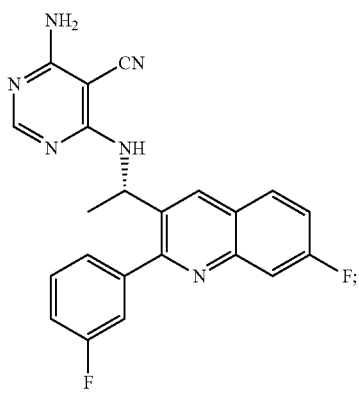

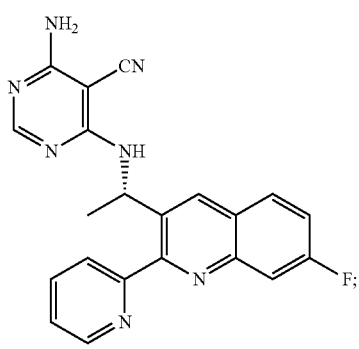 [SMILES: C[C@H](Nc1ncnc(N)c1C#N)c1cc2ccc(F)cc2nc1-c1ccccn1]

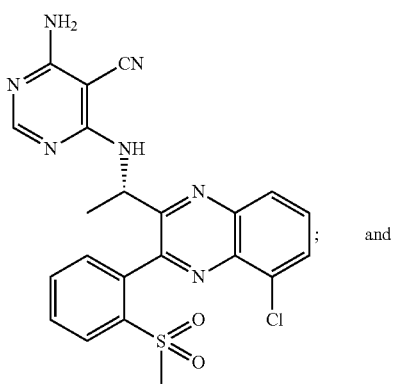 [SMILES: C[C@H](Nc1ncnc(N)c1C#N)c1nc2cccc(Cl)c2nc1-c1ccccc1S(C)(=O)=O]

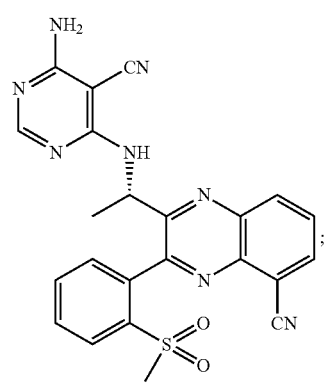 [SMILES: C[C@H](Nc1ncnc(N)c1C#N)c1nc2cccc(C#N)c2nc1-c1ccccc1S(C)(=O)=O]

or any pharmaceutically-acceptable salt thereof.

Another aspect of the invention relates to a method of treating PI3K-mediated conditions or disorders.

In certain embodiments, the PI3K-mediated condition or disorder is selected from rheumatoid arthritis, ankylosing spondylitis, osteoarthritis, psoriatic arthritis, psoriasis, inflammatory diseases, and autoimmune diseases. In other embodiments, the PI3K-mediated condition or disorder is selected from cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease. In still other embodiments, the PI3K-mediated condition or disorder is selected from cancer, colon cancer, glioblastoma, endometrial carcinoma, hepatocellular cancer, lung cancer, melanoma, renal cell carcinoma, thyroid carcinoma, cell lymphoma, lymphoproliferative disorders, small cell lung cancer, squamous cell lung carcinoma, glioma, breast cancer, prostate cancer, ovarian cancer, cervical cancer, and leukemia. In yet another embodiment, the PI3K-mediated condition or disorder is selected from type II diabetes. In still other embodiments, the PI3K-mediated condition or disorder is selected from respiratory diseases, bronchitis, asthma, and chronic obstructive pulmonary disease. In certain embodiments, the subject is a human.

Another aspect of the invention relates to the treatment of rheumatoid arthritis, ankylosing spondylitis, osteoarthritis, psoriatic arthritis, psoriasis, inflammatory diseases or autoimmune diseases comprising the step of administering a compound according to any of the above embodiments.

Another aspect of the invention relates to the treatment of rheumatoid arthritis, ankylosing spondylitis, osteoarthritis, psoriatic arthritis, psoriasis, inflammatory diseases and autoimmune diseases, inflammatory bowel disorders, inflammatory eye disorders, inflammatory or unstable bladder disorders, skin complaints with inflammatory components, chronic inflammatory conditions, autoimmune diseases, systemic lupus erythematosis (SLE), myestenia gravis, rheumatoid arthritis, acute disseminated encephalomyelitis, idiopathic thrombocytopenic purpura, multiples sclerosis, Sjoegren's syndrome and autoimmune hemolytic anemia, allergic conditions and hypersensitivity, comprising the step of administering a compound according to any of the above or below embodiments.

Another aspect of the invention relates to the treatment of cancers that are mediated, dependent on or associated with p110δ activity, comprising the step of administering a compound according to any of the above or below embodiments.

Another aspect of the invention relates to the treatment of cancers are selected from acute myeloid leukaemia, myelodysplastic syndrome, myelo-proliferative diseases, chronic myeloid leukaemia, T-cell acute lymphoblastic leukaemia, B-cell acute lymphoblastic leukaemia, non-hodgkins lymphoma, B-cell lymphoma, solid tumors and breast cancer, comprising the step of administering a compound according to any of the above or below embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of rheumatoid arthritis, ankylosing spondylitis, osteoarthritis, psoriatic arthritis, psoriasis, inflammatory diseases, and autoimmune diseases.

The compounds of this invention may have in general several asymmetric centers and are typically depicted in the form of racemic mixtures. This invention is intended to encompass racemic mixtures, partially racemic mixtures and separate enantiomers and diasteromers.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or trisubstituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl. Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

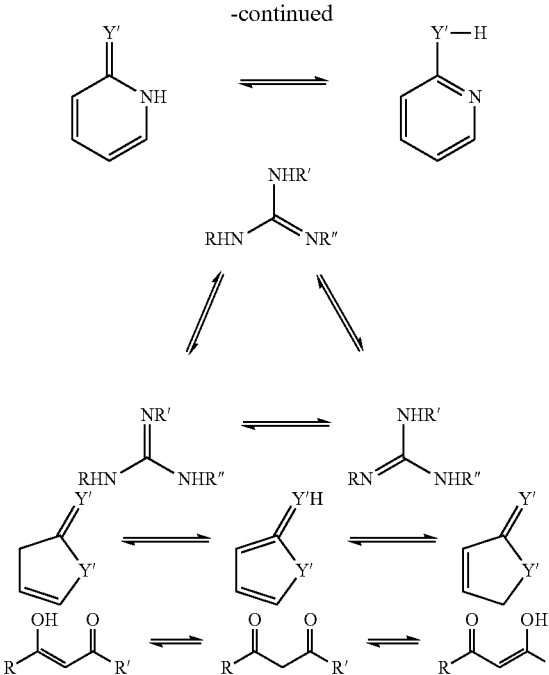

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Experimental
The following abbreviations are used:

| | |
|---|---|
| aq. | aqueous |
| BINAP | 2,2'-bis(diphenylphosphino)-1,1'-binaphthyl |
| cond | concentrated |
| DCM | dichloromethane |
| DMF | N,N-dimethylformamide |
| $Et_2O$ | diethyl ether |
| EtOAc | ethyl acetate |
| EtOH | ethyl alcohol |
| h | hour(s) |
| min | minutes |
| MeOH | methyl alcohol |
| rt | room temperature |
| satd | saturated |
| THF | tetrahydrofuran |

General

Reagents and solvents used below can be obtained from commercial sources. $^1$H-NMR spectra were recorded on a Bruker 400 MHz and 500 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Mass spectrometry results are reported as the ratio of mass over charge, followed by the relative abundance of each ion (in parentheses Electrospray ionization (ESI) mass spectrometry analysis was conducted on a Agilent 1100 series LC/MSD electrospray mass spectrometer. All compounds could be analyzed in the positive ESI mode using acetonitrile:water with 0.1% formic acid as the delivery solvent. Reverse phase analytical HPLC was carried out using a Agilent 1200 series on Agilent Eclipse XDB-C18 5 μm column (4.6×150 mm) as the stationary phase and eluting with acetonitrile:$H_2O$ with 0.1% TFA. Reverse phase semi-prep HPLC was carried out using a Agilent 1100 Series on a Phenomenex Gemini™ 10 μm C18 column (250×21.20 mm) as the stationary phase and eluting with acetonitrile:$H_2O$ with 0.1%. Chiral compounds are purified using Isopropanol/Hexane gradient, AD column. The assignment of chirality is based on the biochemical data.

Example 1

Preparation of 4-amino-6-(((1S)-1-(8-fluoro-2-(2-(methyl-sulfonyl)phenyl)-3-quinolinyl)ethyl)amino)-5-pyrimidinecarbonitrile N-(2-fluorophenyl)cinnamamide

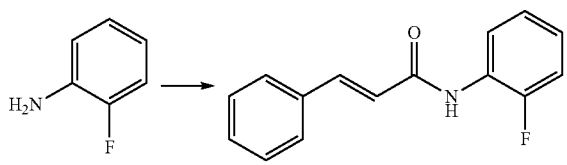 [SMILES: Nc1ccccc1F ; O=C(/C=C/c1ccccc1)Nc1ccccc1F]

To a solution of 2-fluoroaniline (25.0 g, 225 mmol) and potassium carbonate (47 g, 337 mmol) in water (112 mL) and acetone (45 mL) at 0° C. was added cinnamoyl chloride (37.0 g, 225 mmol, 1 eq) in acetone (45 mL) over 2 h. The reaction was stirred for 1 h at 0° C., and quenched into 200 mL of ice-water. The white crystalline solid was filtered and washed with water. The solid was air dried for 2 h, then washed with 400 mL of hexanes. The solid was dried under vacuum overnight to afford N-(2-fluorophenyl)cinnamamide (56 g, 103% yield). $^1$H NMR (400 MHz, CDCl$_3$) δ ppm 8.49 (br t, J=7.8

Hz, 1H), 7.80 (d, J=15.3 Hz, 1H), 7.57 (m, 3H), 7.41 (m, 3H), 7.17 (m, 3H), 6.61 (d, J=15.6 Hz, 1H). Mass Spectrum (ESI) m/e=242.1 (M+1).

8-fluoroquinolin-2(1H)-one

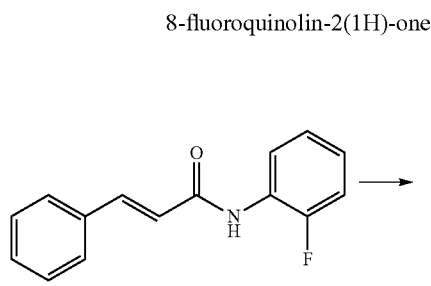

N-(2-Fluorophenyl)cinnamamide (10.5 g, 44 mmol) was dissolved in chloro-benzene (60 mL) and aluminum trichloride (29.0 g, 218 mmol, 5 eq) was added. The reaction was heated to 125° C. for 3 h and then cooled to rt over 45 min. The reaction was poured onto 300 g of ice with stirring, producing a tan solid. The solid was filtered and washed with 100 mL of water and 3×100 mL of hexanes and dried under high vacuum. The solid was extracted with 1 L of DCM and filtered to remove insoluble byproducts. The solvent was removed in vacuo to afford 8-fluoroquinolin-2(1H)-one. $^1$H NMR (400 MHz, CDCl$_3$) δ ppm 10.95 (br s, 1H), 7.77 (dd, J=9.8, 1.6 Hz, 1H), 7.35 (d, J=7.8 Hz, 1H), 7.27 (ddd, J=10.2, 7.8, 1.2 Hz, 1H), 7.14 (td, J=8.0, 5.1 Hz, 1H), 6.76 (d, J=9.4 Hz, 1H).

2-chloro-8-fluoroquinoline

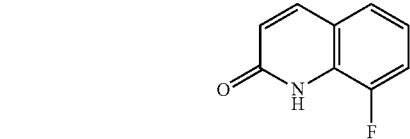

8-Fluoroquinolin-2(1H)-one (26.0 g, 159 mmol) was slurried with phosphoryl trichloride (163 ml, 1.73 mol, 11 eq) and heated to 125° C. for 2 h. The reaction was cooled to rt and poured onto 1.2 L of ice water with vigorous stirring. When the mixture had cooled to rt, the orange solid was filtered and washed with water and dried under vacuum overnight to afford 27 g of crude material. The crude material was recrystallized from hexanes by dissolving in ~700 mL of hexanes at reflux and decanting away from residual tar. The hexane solution was cooled to 0° C. and the precipitate 2-chloro-8-fluoroquinoline was filtered. The mother liquor was concentrated in vacuo and recrystallized from hexanes to obtain a second crop of 2-chloro-8-fluoroquinoline (21.3 g, 74% total yield).

$^1$H NMR (400 MHz, CDCl$_3$) δ ppm 8.14 (dd, J=8.6, 1.2 Hz, 1H), 7.62 (br d, 1H), 7.52 (td, J=7.8, 4.7 Hz, 1H), 7.45 (m, 2H).

1-(2-chloro-8-fluoroquinolin-3-yl)ethanol

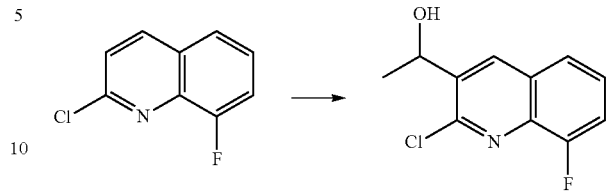

2-Chloro-8-fluoroquinoline (5.00 g, 27.5 mmol) was dissolved in THF (60 mL) and cooled to −78° C. To this solution was added freshly prepared and titrated lithium diisopropylamide (1M solution in THF, 30 mL, 30 mmol, 1.1 eq) over 5 min. The reaction was allowed to stir at −78° C. for 20 min, after which time acetaldehyde (2.3 mL, 41.3 mmol, 1.5 eq.) was added via syringe over 30 seconds (exothermic). After 30 min at −78° C., the reaction was quenched with 50% saturated NH$_4$Cl solution and diluted with EtOAc. The layers were separated and washed with brine, dried over MgSO$_4$, and filtered. The crude reaction mixture was deposited on 30 g of silica gel and passed through a plug of 60 g of silica gel, eluted with 8:2 hexanes:EtOAc. Fractions containing product and a closely (second) eluting regioisomer were collected. The fractions were concentrated and the crude solid was slurried in 140 mL of 9:1 hexanes:EtOAc at reflux for 30 min. After cooling to rt, the solid was filtered and washed with a small amount of cold 9:1 hexanes:EtOAc to afford pure 1-(2-chloro-8-fluoroquinolin-3-yl)ethanol (3.1 g, 13.7 mmol, 50% yield). $^1$H NMR (400 MHz, CDCl$_3$) δ ppm 8.43 (br s, 1H), 7.64 (td, J=7.8, 5.1 Hz, 1H), 7.41 (ddd, J=10.2, 7.4, 1.2 Hz, 1H), 5.39 (qdd, J=6.3, 3.9, 0.8 Hz, 1H), 2.22 (d, J=3.9 Hz, 1H), 1.62 (d, J=6.3 Hz, 3H).

1-(2-chloro-8-fluoroquinolin-3-yl)ethanone

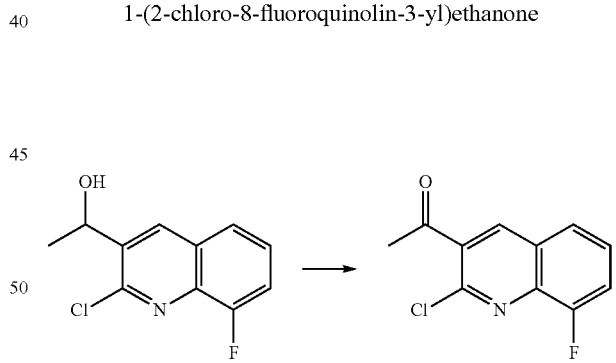

To a round-bottomed flask containing toluene (183 mL) was added 1-(2-chloro-8-fluoroquinolin-3-yl)ethanol (6.20 g, 27.5 mmol) and manganese dioxide (19.1 g, 220 mmol, 8 eq). The reaction was heated to reflux for 2 h, cooled to rt, filtered and concentrated. The product was diluted with hexanes and filtered to give as a white solid 1-(2-chloro-8-fluoroquinolin-3-yl)ethanone (4.43 g, 72% yield). $^1$H NMR (400 MHz, CDCl$_3$) δ ppm 8.40 (d, J=1.6 Hz, 1H), 7.71 (br d, J=8.2 Hz, 1H), 7.56 (td, J=7.8, 5.1 Hz, 1H), 7.54 (ddd, J=9.8, 7.8, 1.6 Hz, 1H). Mass Spectrum (ESI) m/e=223.9 (M+1).

(R)-1-(2-chloro-8-fluoroquinolin-3-yl)ethanol

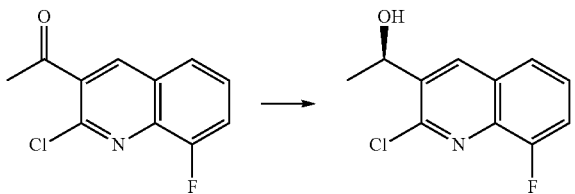

In a round bottomed flask was dissolved (+)-dip-chloride (tm) (17.5 g, 540 mmol, 2.2 eq) in anhydrous THF (200 mL) and the solution was cooled to −55° C. (using a dry ice/MeCN bath). To this solution was added 1-(2-chloro-8-fluoroquinolin-3-yl)ethanone (5.50 g, 24.5 mmol) as a solution in THF (50 mL). The reaction was allowed to warm to rt slowly overnight. After this time the reaction was quenched with 10 mL acetone and 100 mL of 10% $Na_2CO_3$ and allowed to stir for 2 h at rt. Ethyl acetate (750 mL) was added and the layers were separated. The organic phase was washed 3× with a 50% saturated sodium bicarbonate solution and once with brine. The organic layer was dried over $MgSO_4$, filtered, and concentrated. The crude material was concentrated under high vacuum at 75° C. to remove pinene. The residue was slurried in 150 mL of hexanes and 150 mL of water for 3 h at rt. A white precipitate formed and was filtered and dried to afford 4.9 g of 98% ee product. The solid was dissolved in 25 mL of boiling EtOAc and 25 mL of hot hexanes was added to form a precipitate at reflux. The mixture was cooled to −15° C., filtered, and washed with cold 9:1 hexanes:EtOAc to afford (R)-1-(2-chloro-8-fluoroquinolin-3-yl)ethanol (4.07 g, 73% yield). Chiral HPLC (10% IPA in hexanes, chiralcel AD-H shows product to be >99.9% ee. Desired enantiomer elutes at 9.6 min, undesired enantiomer elutes at 8.1 min. $^1$H NMR (400 MHz, $CDCl_3$) δ ppm 8.43 (br s), 7.64 (br d, J=8.2 Hz, 1H), 7.50 (td, J=7.8, 4.7 Hz, 1H), 7.41 (ddd, J=10.2, 7.8, 1.2 Hz, 1H), 5.40 (qd, J=5.9, 0.8 Hz, 1H), 2.22 (br s, 1H), 1.62 (d, J=6.3 Hz, 3H). Mass Spectrum (ESI) m/e=226.0 (M+1).

(S)-2-(1-(2-chloro-8-fluoroquinolin-3-yl)ethyl)isoindoline-1,3-dione

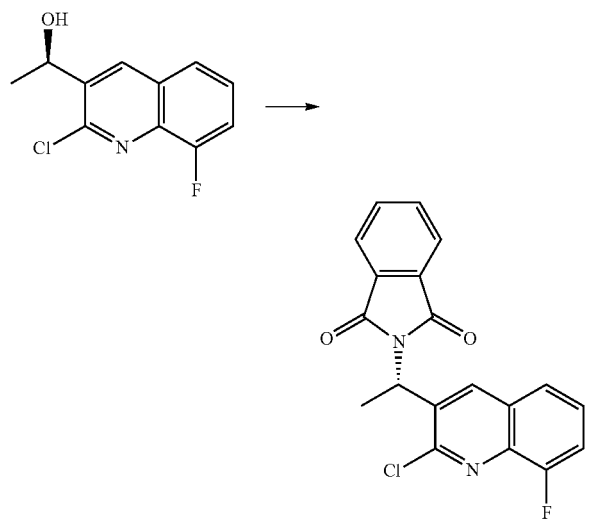

In a round bottomed flask was combined phthalimide (6.38 g, 43.3 mmol), triphenylphosphine (1.14 g, 43.3 mmol), and (R)-1-(2-chloro-8-fluoroquinolin-3-yl)ethanol (8.15 g, 36.2 mmol) in THF (240 mL). The solution was cooled to 0° C. and diisopropylazodicarboxylate (DIAD, 8.5 mL, 43.3 mmol) was added dropwise. The reaction was allowed to warm to rt overnight. The reaction was concentrated to a volume of ~100 mL and diluted with 1 L of $Et_2O$ and 200 mL of water. The layers were separated and the aqueous layer was back extracted with 200 mL of $Et_2O$. The combined organic layers were washed with 160 mL of brine, dried over $MgSO_4$, filtered, and concentrated. Column chromatography using 100% DCM afforded (S)-2-(1-(2-chloro-8-fluoroquinolin-3-yl)ethyl)-isoindoline-1,3-dione (10.5 g, 82% yield). $^1$H NMR (400 MHz, $CDCl_3$) δ ppm 8.60 (br s, 1H), 7.74 (m, 2H), 7.64 (m, 3H), 7.45 (td, J=7.8, 4.9 Hz, 1H), 7.35 (ddd, J=10.2, 7.8, 1.2 Hz, 1H), 5.89 (q, J=7.2 Hz, 1H), 1.90 (d, J=7.0 Hz, 3H).

2-((1S)-1-(8-fluoro-2-(2-(methylthio)phenyl)quinolin-3-yl)ethyl)isoindoline-1,3-dione

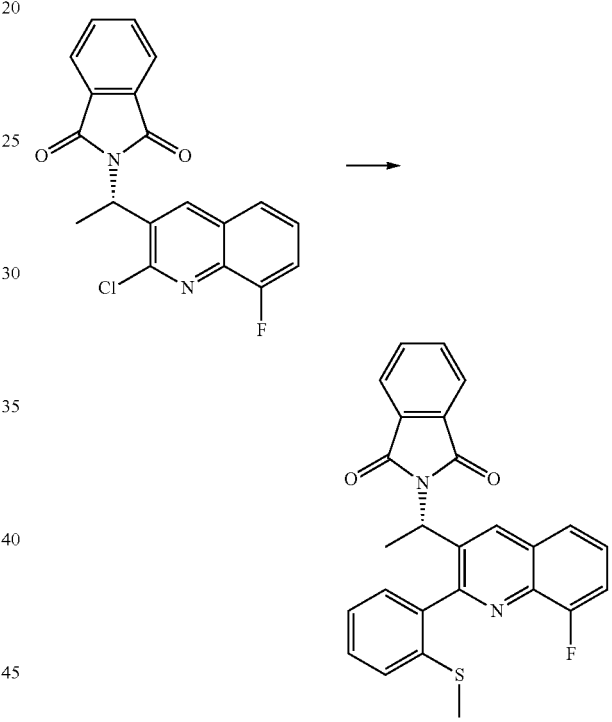

(S)-2-(1-(2-Chloro-8-fluoroquinolin-3-yl)ethyl)isoindoline-1,3-dione (14.0 g, 39.5 mmol), 2-(methylthio)phenylboronic acid (9.95 g, 59.2 mmol), and potassium carbonate (16.4 g, 118 mmol) were combined in 300 mL of anhydrous DMF under an atmosphere of $N_2$. The solution was sparged with $N_2$ for ~5 min before adding $PdCl_2(dppf)CH_2Cl_2$ (3.22 g, 3.95 mmol). The solution was heated at 100° C. for 3 h, and then cooled to 50° C. The solution was concentrated under vacuum to give a brownish residue, which was diluted with EtOAc (600 mL). The organic layers were then washed with $H_2O$ (3×80 mL), followed by brine (1×100 mL). The combined aq. layers were extracted with DCM (3×200 mL). The combined organic layers were dried over $MgSO_4$ and then concentrated under vacuum. The residue obtained was purified by silica gel flash chromatography eluting with a gradient of 20% hexane to 40% EtOAc/hexane. The fractions containing the pure product were combined and concentrated under vacuum to give 2-((1S)-1-(8-fluoro-2-(2-(methylthio)phenyl)quinolin-3-yl)ethyl)isoindoline-1,3-dione (14.6 g, 33.0 mmol, 84% yield) as a light yellow foam. The proton NMR reflects a 53/47 ratio of atropisomers at 25° C. ¹H NMR (500 MHz, CDCl₃) δ ppm 8.71 (br s, 0.53H), 8.65 (br s, 0.47H), 7.79 (m, 1H), 7.66 (s, 4H), 7.55 (m, 1H), 7.45-7.27 (series of m, 3.6; H), 6.87 (m, 1.4H), 5.70 (q J=6.4 Hz, 0.47H), 5.63 (q, J=6.8 Hz, 0.53H), 2.47 (br s, 1.4H), 1.91 (m, 3H), 1.52 (br s, 1.6H). Mass Spectrum (ESI) m/e=443.2 (M+1).

2-((1S)-1-(8-fluoro-2-(2-(methylsulfonyl)phenyl)-3-quinolinyl)ethyl)-1H-isoindole-1,3(2H)-dione

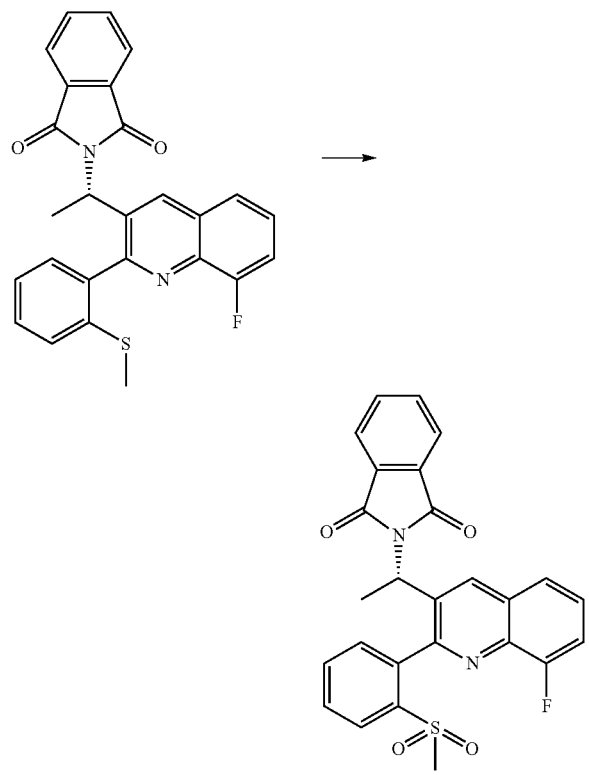

To 70 mL of DCM was added 13.56 g (1.2 g/1 mmol of substrate) of wet Montmorillonite (~0.2 g H₂O/1 g of clay), and oxone (17.37 g, 28.2 mmol)¹. To this suspension was added a solution of 2-((1S)-1-(8-fluoro-2-(2-(methylthio)phenyl)quinolin-3-yl)ethyl)isoindoline-1,3-dione (5.0 g, 11.3 mmol) dissolved in DCM (10 mL). The slurry was stirred at rt for 72 h and then filtered through a fitted funnel. The solids were washed with DCM (~600 mL) and the filtrates were concentrated under vacuum to give 2-((1S)-1-(8-fluoro-2-(2-(methylsulfonyl)phenyl)-3-quinolinyl)ethyl)-1H-isoindole-1,3(2H)-dione 7.11 g (97%) as a light yellow solid. The proton NMR reflects a 59/41 ratio of atropisomers at 25° C. ¹H-NMR (500 MHz, CDCl₃) δ ppm 8.86 (s, 0.59H), 8.79 (s, 0.41H), 8.26 (d, J=7.8 Hz, 0.41H), 8.04 (d, J=7.8 Hz, 0.59H), 7.89-7.36 (series of m, 9.6H), 7.20 (d, J=7.6 Hz, 0.41H), 5.70 (q, J=7.1 Hz, 0.59H), 5.54 (q, J=7.3 Hz, 0.41H), 3.19 (s, 1.75H), 3.15 (s, 1.25H), 1.98 (d, J=7.3 Hz, 1.75H), 1.85 (d, J=7.1 Hz, 1.25H). Mass Spectrum (ESI) m/e=475.0 (M+1).

1. Hirano, M.; Tomaru, J.; Morimoto, T. *Bull. Chem. Soc. Jpn.*, 1991, 64, 3752-54.

(1S)-1-(8-fluoro-2-(2-(methylsulfonyl)phenyl)-3-quinolinyl)ethanamine

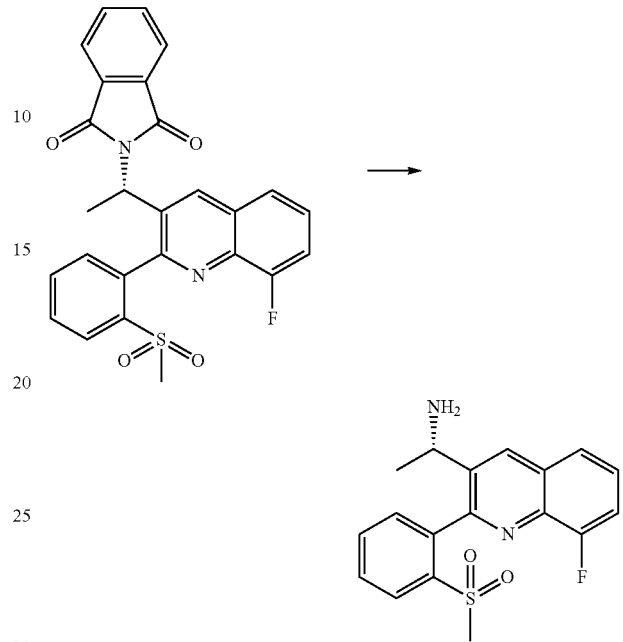

2-((1S)-1-(8-Fluoro-2-(2-(methylsulfonyl)phenyl)quinolin-3-yl)ethyl)isoindoline-1,3-dione (9.10 g, 19.2 mmol), and hydrazine hydrate (9.32 mL, 192 mmol) were added to EtOH (190 mL). After heating at 65° C. for 3 h, the resultant slurry was cooled to rt, diluted with 900 mL of EtOAc, and filtered through a fritted funnel. The filtrate was washed with H₂O (3×200 mL), brine(1×200 mL) and then dried over MgSO₄ before being concentrated under vacuum to give (1S)-1-(8-fluoro-2-(2-(methylsulfonyl)phenyl)quinolin-3-yl)ethanamine (6.06 g, 17.6 mmol, 92% yield) as a light orange solid. The proton NMR reflects a 73/27 ratio of atropisomers at 25° C. ¹H NMR (500 MHz, CDCl₃) δ ppm 8.55 (d, J=1.5 Hz, 0.73H), 8.50 (d, J=1.5 Hz, 0.27H), 8.26 (dd, J=8.1, 1.2 Hz, 0.27H), 8.23 (dq, J=7.8 1.2 Hz, 0.73H), 7.73 (m, 3H), 7.52 (m, 1.27H), 7.40 (m, 1.73H), 4.16 (q, J=6.6 Hz, 0.27H), 4.03 (q, J=6.4 Hz, 0.73H), 3.36 (s, 0.79H), 3.17 (s, 2.21H), 1.36 (m, 3H). Mass Spectrum (ESI) m/e=345.2 (M+1).

4-amino-6-(((1S)-1-(8-fluoro-2-(2-(methylsulfonyl)phenyl)-3-quinolinyl)-ethyl)amino)-5-pyrimidinecarbonitrile

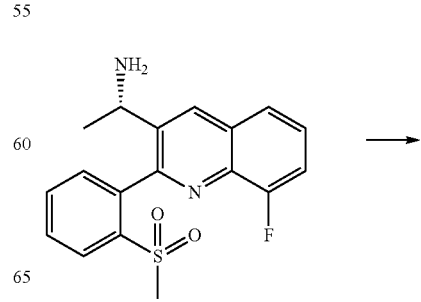

-continued

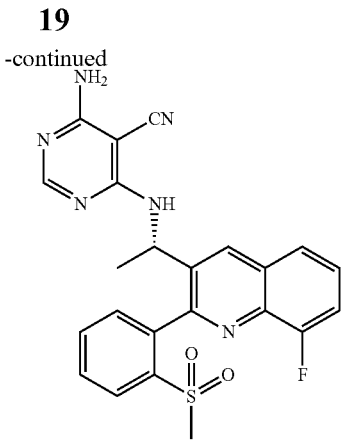

(1S)-1-(8-Fluoro-2-(2-(methylsulfonyl)phenyl)quinolin-3-yl)ethanamine (9.16 g, 26.6 mmol), N-ethyl-N-isopropyl-propan-2-amine (13.7 mL, 80 mmol), and 4-amino-6-chloro-pyrimidine-5-carbonitrile (4.32 g, 27.9 mmol) were combined in n-butanol (67 mL) and then heated to 110° C. under an atmosphere of $N_2$. After 3 h at 110° C., the temperature of the reaction was increased to 120° C. for 2 h. After cooling in an ice bath, the mixture was filtered leaving 14 g of a brownish solid. The filtrate was heated to 120° C. for 3 h, cooled to 40° C. and concentrated under vacuum leaving a brown oil. The oil and solids were combined and purified on a silica gel flash column eluting with 2% MeOH/DCM. The fractions containing the pure product were combined and concentrated under vacuum to give a light yellowish solid. The fractions containing the impure product were combined and purified on a silica gel flash column eluting with a gradient of 1.5% MeOH/DCM to 2% MeOH/DCM. The fractions containing the pure product were combined and concentrated under vacuum to give a light yellowish solid. The combined pure solids were dissolved in EtOH with heating (~60° C.), and then concentrated under vacuum, repeated the dissolution into EtOH followed by concentration under vacuum. The solids obtained were then dried on the vacuum line at 120° C. until residual ethanol was below 0.5% by weight. The solid obtained was 4-amino-6-(((1S)-1-(8-fluoro-2-(2-(methylsulfonyl)phenyl)-3-quinolinyl)ethyl)-amino)-5-pyrimidinecarbonitrile, 10.3 g (84% yield). The proton NMR reflects a 87/13 ratio of atropisomers at 25° C. $^1$H NMR (500 MHz, DMSO-d6) δ ppm 8.80 (br s, 0.13H), 8.58 (br s, 0.87H), 8.13 (dd, J=7.7, 1.2 Hz, 0.87H), 7.95-7.52 (series of m, 8H), 7.30-6.99 (br m, 2H), 6.82 (d, J=8.3 Hz, 1H), 5.62 (quintet, J=6.9 Hz, 0.13H), 5.22 (quintet, J=6.9 Hz, 0.87H), 3.37 (s, 2.57H), 3.31 9 s, 0.43H), 1.60 (d, J=6.9 Hz, 0.4H), 1.35 (d, J=6.9 Hz, 2.6H). Mass Spectrum (ESI) m/e=463.1 (M+1).

Example 2

Preparation of (S)-4-amino-6-(1-(7-fluoro-2-(2-(methylsulfonyl)-phenyl) quinolin-3-yl)ethyl)amino) pyrimidine-5-carbonitrile 2-chloro-7-fluoroquinoline-3-carbaldehyde

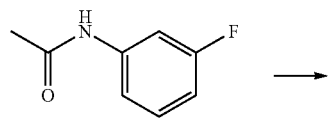

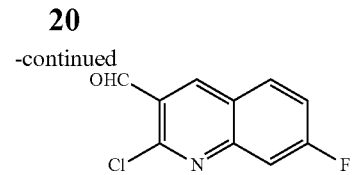

POCl$_3$ (0.837 L, 9.17 mmol) was added dropwise to DMF (253 mL, 3.28 mmol) in a three-necked flask equipped with mechanical stirrer at 0° C. The semi-solid mixture was stirred at rt for 30 min and N-(3-fluorophenyl)acetamide (200 g, 1.31 mol) was added in one portion. The resulting mixture was heated at 75° C. over night. After cooling to rt, the reaction mixture was poured carefully into ice-water (9 kg). The resulted solid was filtered, washed with water, NaHCO$_3$, and dried in the air. The crude mixture (200 g, 73%) was recrystallized in EtOAc (5 L) to give 2-chloro-7-fluoroquinoline-3-carbaldehyde as off white needles (150 g). Mass Spectrum (ESI) m/e=210 (M+1).

1-(2-chloro-7-fluoroquinolin-3-yl)ethanol

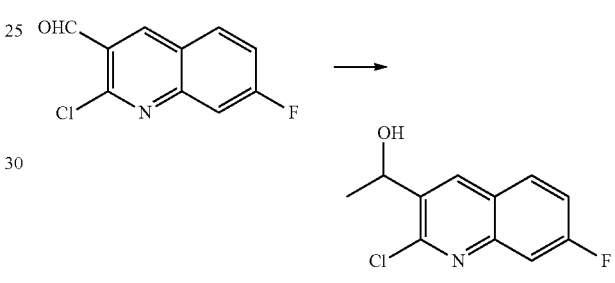

A suspension of 2-chloro-7-fluoroquinoline-3-carbaldehyde (44.7 g, 213 mmol) in THF (600 mL) was treated with MeMgBr (78.0 mL, 234 mmol 1.1 eq) at −20° C. After stirring overnight, the reaction was quenched with NH$_4$Cl solution and extracted with Et$_2$O (300 mL and 100 mL). The organic layers were washed with water, brine, dried over Na$_2$SO$_4$, concentrated and recrystallized from EtOAc (100 mL) and hexane (1 L). A pale yellow solid of 1-(2-chloro-7-fluoroquinolin-3-yl)-ethanol was obtained (41 g, 85%). Mass Spectrum (ESI) m/e=226 (M+1).

1-(2-chloro-7-fluoroquinolin-3-yl)ethanone

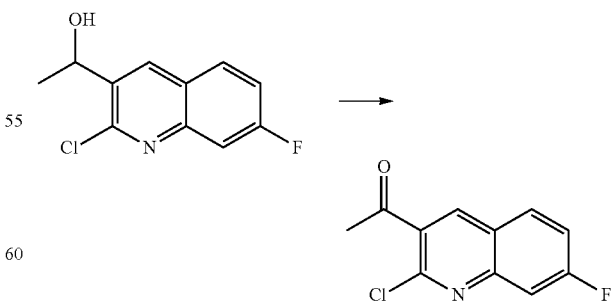

1-(2-Chloro-7-fluoroquinolin-3-yl)ethanol (7.7 g, 34 mmol), MnO$_2$ (30 g, 10 eq) and Toluene (200 mL) were heated to reflux for 2 h. LC-MS showed completion of the reaction. Filtration followed with removal of solvent gave an off-white solid of 1-(2-chloro-7-fluoroquinolin-3-yl)ethanone (6.2 g, 81%). Mass Spectrum (ESI) m/e=224 (M+1).

(R)-1-(2-chloro-7-fluoroquinolin-3-yl)ethanol

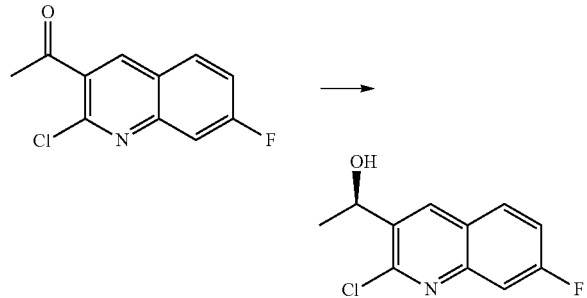

A solution of 1-(2-chloro-7-fluoroquinolin-3-yl)ethanone (164 g, 733 mmol) in THF (1.34 L) was added to a solution of (+)-DIP-Cl (517.5 g, 2.2 eq) in THF (3.5 L) at −45° C. (dry ice and acetonitrile) dropwise. The reaction was slowly warmed up to rt overnight. The reaction was then quenched with acetone (750 mL) and 10% $Na_2CO_3$ (750 mL) at 0° C. and stirred at rt for 1 h before the addition of EtOAc (3.5 L). The mixture was warmed up to rt and washed with 10% $Na_2CO_3$ and water. The organic layer was dried with brine, concentrated and treated with hexane (1.0 L) and water (1.8 L). The mixture was stirred at rt for 40 min and filtered. The white solid was washed with water and hexane, dried in the air over night (143 g). This material was dried on the roto-evaporator at 60° C. for 4 h under high vacuum (2 mm Hg) to give a white powder of (R)-1-(2-chloro-7-fluoroquinolin-3-yl)ethanol (122 g, 73.7%). Chiral HPLC on AD column (isopropanol in hexane, 10%) showed ee>99%. Mass Spectrum (ESI) m/e=226 (M+1).

S)-2-(1-(2-chloro-7-fluoroquinolin-3-yl)ethyl)isoindoline-1,3-dione

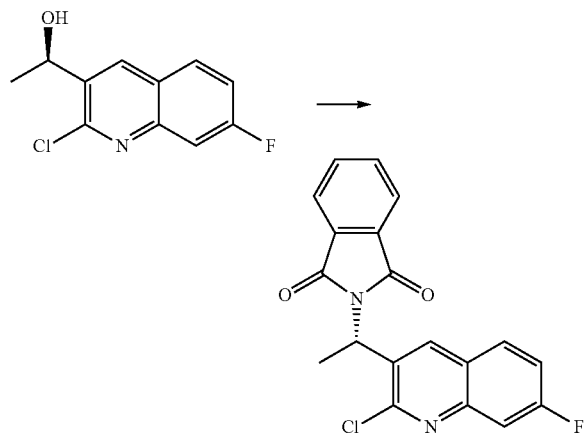

To a mixture of (R)-1-(2-chloro-7-fluoroquinolin-3-yl)ethanol (3.03 g, 13.4 mmol), phthalimide (2.37 g, 1.20 eq) and $PPh_3$ (4.23 g, 1.20 eq) in THF (70 mL) was added DIAD (3.13 mL, 1.20 eq) dropwise at 0° C. The mixture was then stirred at rt overnight before partitioning between EtOAc (200 mL) and water (200 mL). The organic layer was separated, washed with water, brine, dried over $Na_2SO_4$ and concentrated. The residue was purified by column chromatography on silica gel (DCM) to give a white foam of (S)-2-(1-(2-chloro-7-fluoroquinolin-3-yl)ethyl)isoindoline-1,3-dione (3.8 g, 80%). Mass Spectrum (ESI) m/e=355 (M+1).

(S)-tert-butyl (1-(2-chloro-7-fluoroquinolin-3-yl)ethyl)carbamate

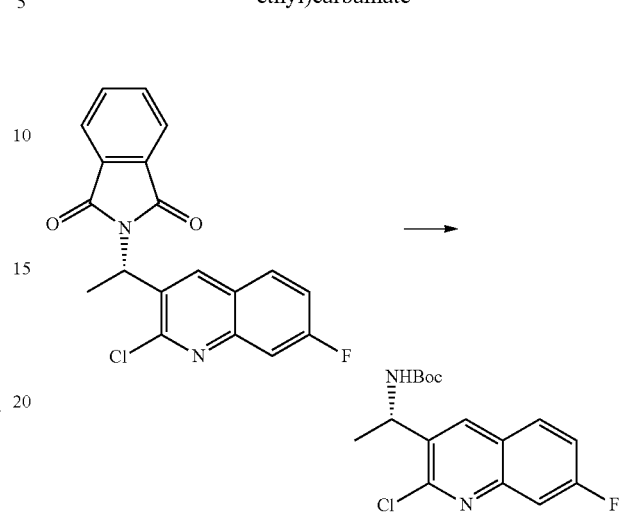

To a solution of (S)-2-(1-(2-chloro-7-fluoroquinolin-3-yl)ethyl)isoindoline-1,3-dione (1.0 g, 2.8 mmol) in EtOH (10 mL) was added dropwise $NH_2NH_2$ (10 eq, 0.88 mL) at rt before warmed up to 90° C. for 30 min. After cooling to rt, the reaction mixture was concentrated, partitioned between EtOAc (20 mL) and water (5 mL). The organic layer was separated, washed with water, brine, dried over $Na_2SO_4$ and concentrated to give a colorless oil, which was dissolved in THF (10 mL) and treated with $BOC_2O$ (1.1 eq, 0.68 g) and TEA (1.0 eq, 0.39 mL) at reflux. After cooling to rt, the reaction mixture was concentrated and purified by column chromatography on silica gel (EtOAc/hexane, 1/9) to give a white solid (S)-tert-butyl (1-(2-chloro-7-fluoroquinolin-3-yl)ethyl)carbamate (0.70 g, 76%). Mass Spectrum (ESI) m/e=325 (M+1).

(S)-tert-butyl (1-(7-fluoro-2-(2-(methylthio)phenyl)quinolin-3-yl)ethyl)-carbamate

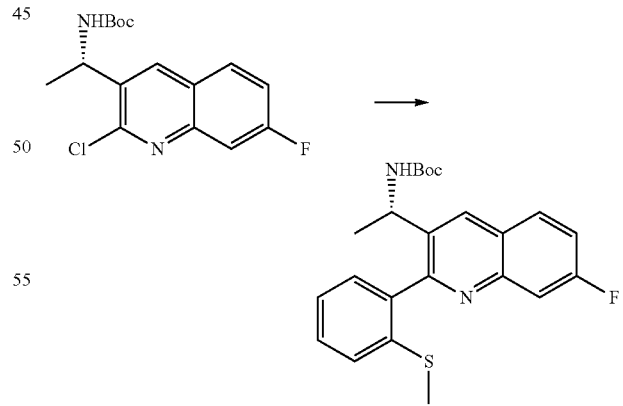

A mixture of (S)-tert-butyl (1-(2-chloro-7-fluoroquinolin-3-yl)ethyl)carbamate (382 mg, 1.2 mmol), 2-(methylthio)phenylboronic acid (257 mg, 1.3 eq), $Na_2CO_3$ (623 mg, 5.0 eq), $Pd(PPh_3)_4$ (93 mg, 5%), MeCN (9 mL) and water (3 mL) was heated to 85° C. under $N_2$ overnight. After cooling to rt, the reaction was partitioned between EtOAc (10 mL) and water (5 mL). The organic layer was separated, washed, dried and concentrated. The residue was purified by column chromatography on silica gel to give a white solid (S)-tert-butyl (1-(7-fluoro-2-(2-(methylthio)phenyl)quinolin-3-yl)ethyl) carbamate (460 mg, 94.8%). Mass Spectrum (ESI) m/e=413 (M+1).

(S)-tert-butyl (1-(7-fluoro-2-(2-(methylsulfonyl)phenyl)quinolin-3-yl)ethyl)-carbamate

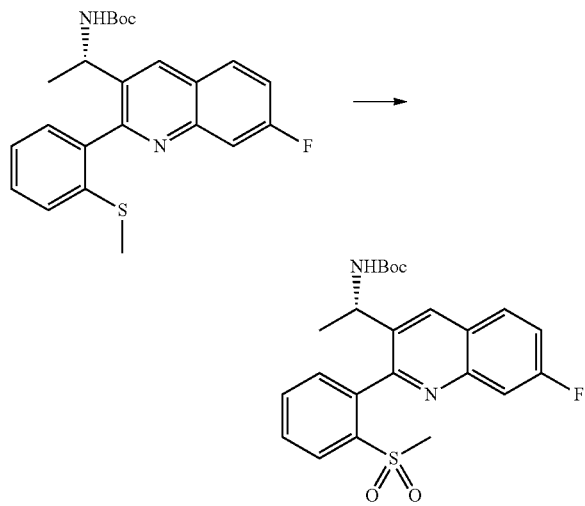

Under an $N_2$ atmosphere, (S)-tert-butyl (1-(7-fluoro-2-(2-(methylthio)phenyl)-quinolin-3-yl)ethyl)carbamate (412 mg, 999 μmol) was dissolved in acetone (3.00 ml, 40.8 mmol) and water (3 mL), and NMO (351 mg, 3.00 mmol) was added followed by $OsO_4$ (12.7 mg, 0.05 mmol). The reaction was allowed to stir at rt overnight. LC-MS showed the reaction not to be complete. The reaction was treated with $OsO_4$ (12.7 mg, 0.05 mmol) again and stirred overnight. LC-MS showed only a trace of the starting reagent. The reaction was quenched by the addition of 5 mL of a saturated sodium thiosulfate solution. The reaction was diluted with EtOAc and washed with 5% $Na_2CO_3$. The organic layer was then washed with brine, dried ($Na_2SO_4$), filtered and concentrated in vacuo. The crude residue was purified eluting with 30% to 60% EtOAc in hexanes to provide a white solid (S)-tert-butyl (1-(7-fluoro-2-(2-(methylsulfonyl)phenyl)quinolin-3-yl)-ethyl)carbamate (440 mg, 99%). Mass Spectrum (ESI) m/e=445 (M+1).

(S)-4-amino-6-((1-(7-fluoro-2-(2-(methylsulfonyl) phenyl)quinolin-3-yl)ethyl)-amino)pyrimidine-5-carbonitrile

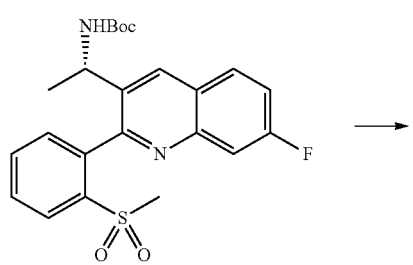

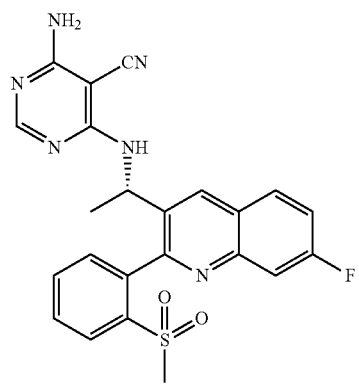

To (S)-tert-butyl (1-(7-fluoro-2-(2-(methylsulfonyl)phenyl)quinolin-3-yl)ethyl)-carbamate (440 mg, 1.0 mmol) was added HCl, 4M (1 mL). The resulting mixture was stirred at rt for 1 h. Solvent was removed and the crude (S)-1-(7-fluoro-2-(2-(methylsulfonyl)phenyl)quinolin-3-yl)ethanamine was used without further workup. A solution of (1S)-1-(7-fluoro-2-(2-(methylsulfonyl)phenyl)-quinolin-3-yl)ethanamine (100 mg, 290 mmol), 4-amino-6-chloropyrimidine-5-carbonitrile (45 mg, 290 μmol) and DIEA (101 μl, 581 mol) in DMF (4 mL) was heated to 100° C. overnight. Solvent was removed under reduce pressure and purified via preparatory. TLC using 3% of MeOH/DCM to afford a white powder of (S)-4-amino-6-((1-(7-fluoro-2-(2-(methylsulfonyl)phenyl)quinolin-3-yl)ethyl)-amino)pyrimidine-5-carbonitrile (6.9 mg, 5.1%). $^1$H NMR (500 MHz, $CD_3OD$) δ ppm 1.51 (d, J=7.09 Hz, 3H) 3.17 (s, 3H) 5.43 (d, J=6.85 Hz, 1H) 7.48 (d, J=2.45 Hz, 1H) 7.60-7.63 (m, 1H) 7.66-7.69 (m, 2H) 7.73 (d, J=1.47 Hz, 1H) 7.81 (s, 1H) 8.07 (dd, J=9.05, 6.11 Hz, 1H) 8.13-8.17 (m, 1H) 8.49 (s, 1H). Mass Spectrum (ESI) m/e=463 (M+1).

Example 3

Preparation of 4-amino-6-((S)-1-(7-fluoro-2-(3-fluorophenyl)-quinolin-3-yl)ethylamino)pyrimidine-5-carbonitrile 2-((S)-1-(7-fluoro-2-(3-fluorophenyl)quinolin-3-yl) ethyl)isoindoline-1,3-dione

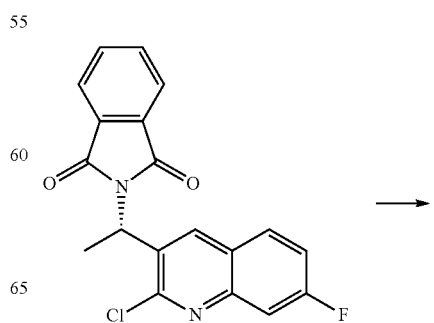

4-amino-6-((S)-1-(7-fluoro-2-(3-fluorophenyl)quinolin-3-yl)ethylamino)-pyrimidine-5-carbonitrile

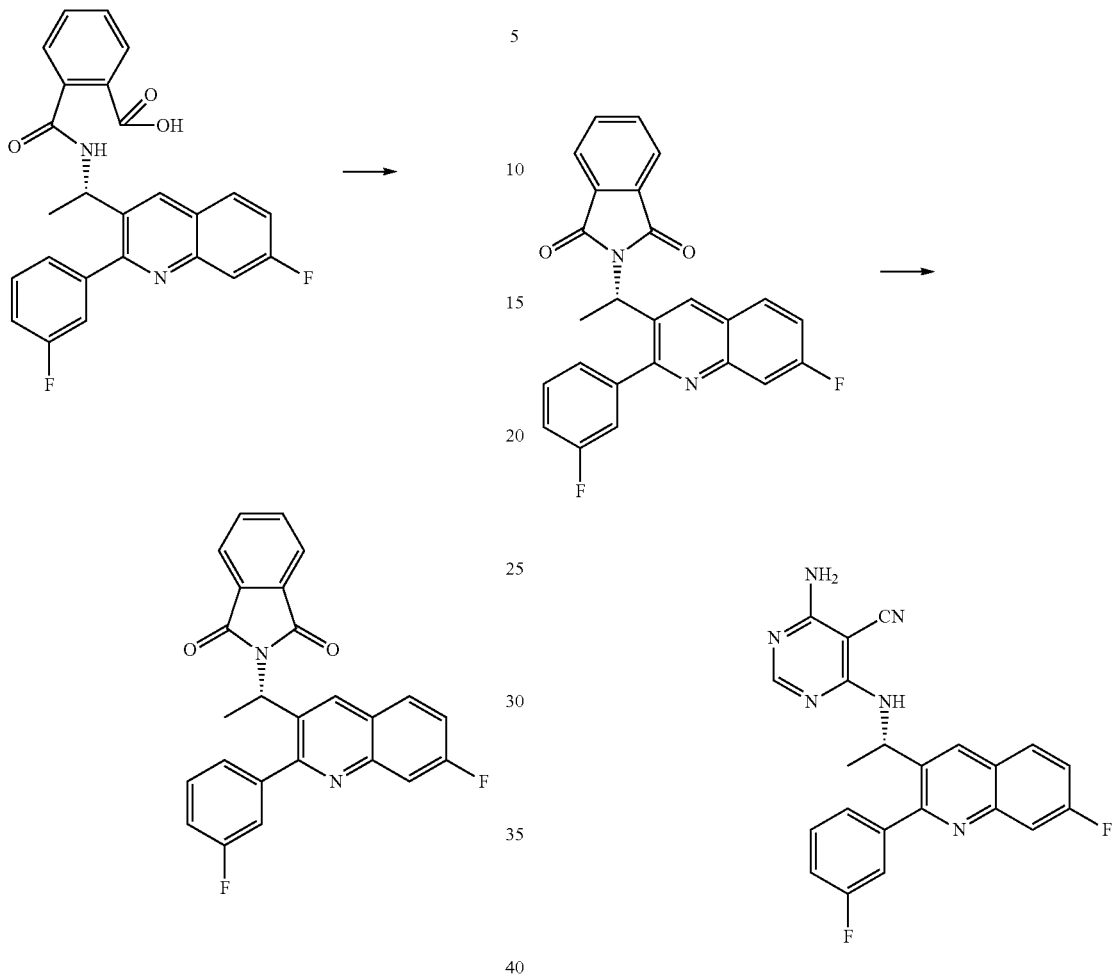

To a solution of (S)-2-(1-(2-chloro-7-fluoroquinolin-3-yl)ethyl)isoindoline-1,3-dione (150 mg, 423 μmol), 3-fluorophenylboronic acid (65 mg, 465 μmol) and sodium carbonate (90 mg, 846 μmol) in MeCN (8 mL) and water (2 mL) was purged with $N_2$ followed by the addition of Pd(PPh$_3$)$_4$ (24 mg, 21 μmol) and the resulting mixture was stirred at 90° C. overnight. The reaction mixture was diluted with EtOAc washed with water, brine and dried over Na$_2$SO$_4$. Purification using preparatory TLC eluted with 100% EtOAc afforded 2-(((S)-1-(7-fluoro-2-(3-fluorophenyl)quinolin-3-yl)ethyl)carbamoyl)benzoic acid (120 mg, 66%). Mass Spectrum (ESI) m/e=433 (M+1). 2-(((S)-1-(7-Fluoro-2-(3-fluorophenyl)-quinolin-3-yl)ethyl)carbamoyl)benzoic acid was dissolved in EtOH (2 mL) and cond HCl (0.1 mL) was added. The resulting solution was heated to 80° C. for 4 h. Solvent was removed and satd NaHCO$_3$ was added to the reaction mixture and extracted with EtOAc. The organic layer was washed with brine, dried over Na$_2$SO$_4$, concentrated and purified via preparatory TLC using 3% MeOH/DCM saturated with NH$_3$ gas to afford a white solid of 2-((S)-1-(7-fluoro-2-(3-fluorophenyl)quinolin-3-yl)ethyl)isoindoline-1,3-dione (85 mg, 49%). Mass Spectrum (ESI) m/e=415 (M+1).

To a solution of 2-((S)-1-(7-fluoro-2-(3-fluorophenyl)quinolin-3-yl)ethyl)-isoindoline-1,3-dione (60.0 mg, 145 μmol) in EtOH (2 mL) was added NH$_2$NH$_2$ (1.0 mL, 1.45 mmol, 10 eq) and the resulting solution was heated to 80° C. for 2 h. A precipitate was filtered away and the filtrate was removed under reduce pressure to afford (1S)-1-(7-fluoro-2-(3-fluorophenyl)quinolin-3-yl)ethanamine To the crude residue of (1S)-1-(7-fluoro-2-(3-fluorophenyl)quinolin-3-yl)-ethanamine in DMF (2 mL) was added 4-amino-6-chloropyrimidine-5-carbonitrile (22 mg, 145 μmol) and DIEA (0.06 mL, 319 μmol). The resulting mixture was heated to 100° C. overnight. Solvent was removed under reduce pressure and purified via preparatory HPLC using 15-60% MeCN/H$_2$O w/0.01% TFA to afford a white solid of 4-amino-6-((S)-1-(7-fluoro-2-(3-fluorophenyl)-quinolin-3-yl)ethylamino)pyrimidine-5-carbonitrile (9.3 mg, 16%). $^1$H NMR (500 MHz, CD$_3$OD) δ ppm 1.63 (d, J=6.85 Hz, 3H) 5.70 (q, J=7.01 Hz, 1H) 7.25-7.34 (m, 1H) 7.44-7.54 (m, 2H) 7.55-7.63 (m, 2H) 7.74 (dd, J=9.78, 2.45 Hz, 1H) 8.05 (s, 1H) 8.18 (dd, J=9.05, 5.87 Hz, 1H) 8.72 (s, 1H). Mass Spectrum (ESI) m/e=403 (M+1).

Example 4

Preparation of (S)-4-amino-6-((1-(7-fluoro-2-(pyridin-2-yl)-quinolin-3-yl)ethyl)amino)pyrimidine-5-carbonitrile 2-((S)-1-(7-fluoro-2-(pyridin-2-yl)quinolin-3-yl)ethyl)isoindoline-1,3-dione

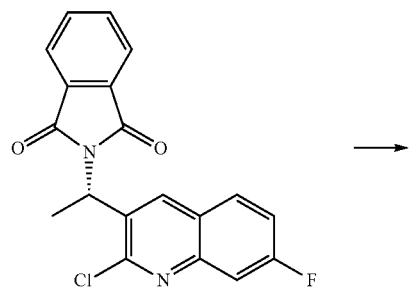

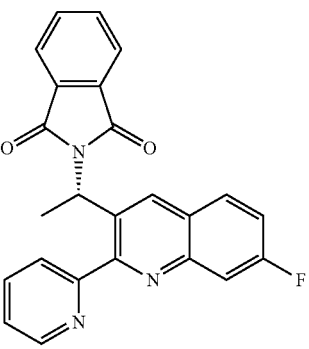

A mixture of (S)-2-(1-(2-chloro-7-fluoroquinolin-3-yl)ethyl)isoindoline-1,3-dione (85.6 g, 241 mmol), Pd(PPh$_3$)$_4$ (14 g, 12 mmol, 0.05 eq) and 2-(tributylstannyl)-pyridine (107 g, 289 mmol, 1.2 eq) in dioxane (3.0 L) was heated to 90° C. under N$_2$. After stirring overnight, LC-MS showed 30% completion. The reaction mixture was heated to 101° C. for additional 2 days. The reaction mixture was then cooled to rt, decanted and the remaining 200 mL solution filtered to remove Pd residue. The combined solvents were concentrated to 300 mL and filtered to give a tan solid, which was washed with EtOAc/hexane (1/1) and dried to provide (82.1 g). The mother liquor was concentrated to 100 mL and treated with EtOAc/hexane, 1/1 (200 mL) to give a second crop of product (2.2 g). Overall a tan solid of 2-((S)-1-(7-fluoro-2-(pyridin-2-yl)quinolin-3-yl)ethyl)isoindoline-1,3-dione was obtained (84.3 g, 88%). Mass Spectrum (ESI) m/e=398 (M+1).

(S)-1-(7-fluoro-2-(pyridin-2-yl)quinolin-3-yl)ethanamine

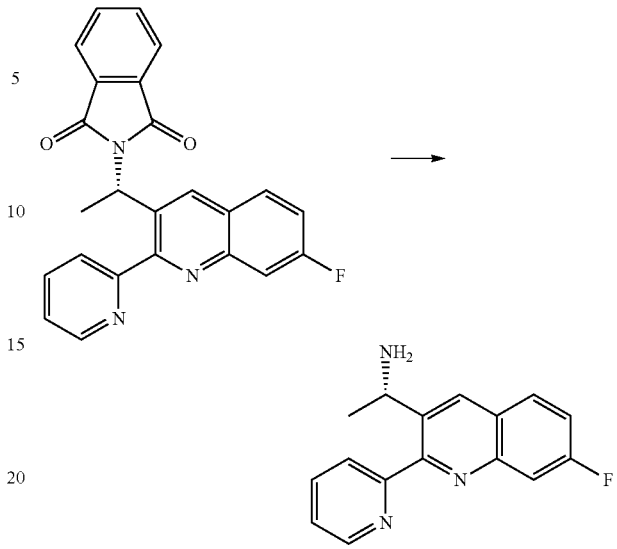

To a slurried 2-((S)-1-(7-fluoro-2-(pyridin-2-yl)quinolin-3-yl)ethyl)isoindoline-1,3-dione (2.1 g, 5.3 mmol) in anhydrous ethanol (15 mL) was added NH$_2$NH$_2$ (0.85 g, 26 mmol) dropwise over 5 minutes. The reaction mixture was heated to 90° C. for 30 min and cooled to rt. The reaction mixture was filtered and washed with EtOAc. The resulting EtOAc solution was washed with water, brine and dried over Na$_2$SO$_4$. Removal of solvents gave a tan oil of (S)-1-(7-fluoro-2-(pyridin-2-yl)quinolin-3-yl)ethanamine (1 g, 71%). Mass Spectrum (ESI) m/e=468 (M+1).

4-amino-6-((S)-1-(7-fluoro-2-(pyridin-2-yl)quinolin-3-yl)ethylamino)-pyrimidine-5-carbonitrile

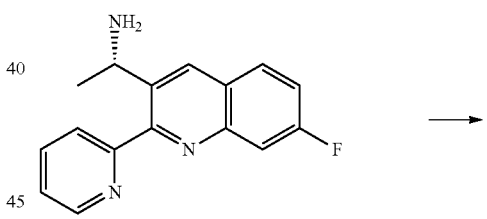

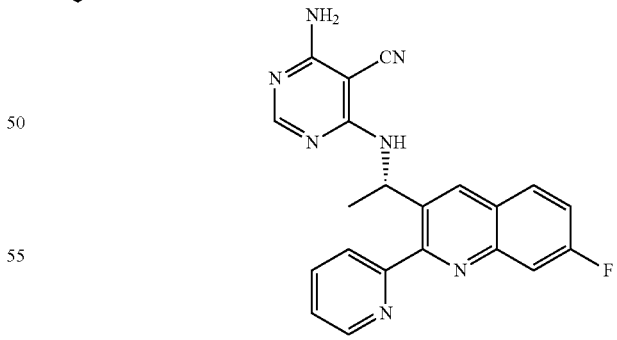

A mixture of (S)-1-(7-fluoro-2-(pyridin-2-yl)quinolin-3-yl)ethanamine (85 mg, 0.32 mmol), 4,6-dichloro-5-cyanopyrimidine (55 mg, 0.32 mmol, 1.0 eq) and N, N-diisopropylethylamine (68 μl, 0.38 mmol, 1.2 eq) in THF (3 mL) was stirred at rt for 30 min before heating to 50° C. After 4 h, the mixture was concentrated and purified by column chromatography (EtOAc/1/1) to give a white solid, which was treated with saturated NH$_3$ in dioxane (3 mL) in sealed tube at 110° C. overnight. The reaction mixture was concentrated and purified by reverse phase HPLC (MeCN/H$_2$O/0.1% TFA) and lyophilized to give a white powder 4-amino-6-((S)-1-(7-fluoro-2-(pyridin-2-yl)quinolin-3-yl)ethylamino)pyrimidine-5-carbonitrile (19 mg, 15%). $^1$H NMR (500 MHz, CD$_3$OD) δ ppm 1.78 (d, J=6.85 Hz, 3H) 5.82 (q, J=6.85 Hz, 1H) 7.71 (td, J=8.80, 2.45 Hz, 1H) 7.89 (dd, J=9.66, 2.32 Hz, 1H) 8.10 (ddd, J=7.83, 5.62, 0.98 Hz, 1H) 8.19 (s, 1H) 8.27 (dd, J=9.05, 5.87 Hz, 1H) 8.45 (d, J=7.83 Hz, 1H) 8.63 (td, J=7.95, 1.47 Hz, 1H) 8.94 (s, 1H) 9.03-9.09 (m, 1H). Mass Spectrum (ESI) m/e=386 (M+1).

Example 5

Preparation of (S)-4-amino-6-((1-(5-chloro-3-(2-(methylsulfonyl)-phenyl)quinoxalin-2-yl)ethyl)amino)pyrimidine-5-carbonitrile 2-((3-chloro-2-nitrophenyl)amino)butanoic acid

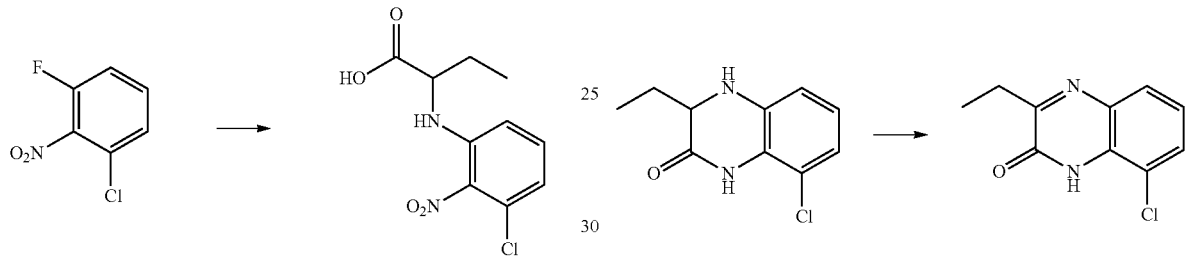

A mixture of 1-chloro-3-fluoro-2-nitrobenzene (2.00 Kg, 11.4 mol), 2-aminobutyric acid (1.22 kg, 11.8 mol) and K$_2$CO$_3$ (1.58 Kg, 11.4 mol) in anhydrous DMSO (4.2 L) was heated at 80° C. for 16 h (after the reaction initiated, the internal temperature went up to 110° C.). At this time LC-MS analysis showed that the reaction was complete. After cooling to rt, the reaction mixture was carefully poured into water (10 L) with vigorous stirring. The aq. layer was washed with methyl tert-butyl ether (2×5 L) to remove organic impurities. The aq. layer was then acidified to pH ~1.5 with cond HCl to give an orange solid. The orange solid was collected by filtration, washed with water (2×4 L) and air-dried to give 2-((3-chloro-2-nitrophenyl)amino)butanoic acid (2.85 Kg), which was used as such in the next step. $^1$H NMR (DMSO-d$_6$) δ ppm 7.35 (t, J=8.3 Hz, 1H), 6.82-6.91 (m, 2H), 6.25 (d, J=7.6 Hz, 1H), 4.14 (td, J=7.4, 5.4 Hz, 1H), 3.4 (br. s., 1H), 1.74-1.92 (m, 2H), 0.88 (t, J=7.4 Hz, 3H). Mass Spectrum (ESI) m/z=259.2 (M+1).

8-chloro-3-ethyl-3,4-dihydroquinoxalin-2(1H)-one

To a solution of 2-((3-chloro-2-nitrophenyl)amino)butanoic acid (1.5 Kg, 5.8 mol), 4 N aq. HCl (4.35 L, 17.4 mol) and EtOH (5.3 L) was added SnCl$_2$.2H$_2$O (3.93 Kg, 17.4 mol). The reaction mixture was heated to reflux for 5 h. At this time LC-MS analysis showed that the reaction was complete. After cooling to rt the reaction mixture was evaporated under reduced pressure. The resulting residue was cooled to 0° C. using an ice-water bath and an aqueous solution of 10 N KOH (12 L, 180 mol) was carefully added with vigorous stirring. After filtration to remove insoluble solids, the filtrate was extracted with DCM (2×10 L) washed with water, brine, dried over anhydrous Na$_2$SO$_4$, and evaporated under reduced pressure to give 8-chloro-3-ethyl-3,4-dihydroquinoxalin-2(1H)-one (1.1 Kg) as a yellow solid, which was used without further purification. $^1$H NMR (DMSO-d$_6$) δ ppm 9.70 (s, 1H), 6.65-6.83 (m, 3H), 6.31-6.44 (m, 1H), 3.66-3.72 (m, 1H), 1.53-1.71 (m, 2H), 0.92 (t, J=7.4 Hz, 3H). Mass Spectrum (ESI) m/z=211.2 (M+1).

8-chloro-3-ethylquinoxalin-2(1H)-one

To a solution of 8-chloro-3-ethyl-3,4-dihydroquinoxalin-2(1H)-one (1.30 Kg, 6.17 mol) in anhydrous 1,4-dioxane (15 L) was added DDQ (1.47 Kg, 6.48 mol). The reaction mixture was stirred for 3 h (the internal temperature went up to 45° C. after DDQ addition). After this time LC-MS analysis showed that the reaction was complete. The mixture was evaporated under reduced pressure to give a brown residue. To this residue was added 2M aqueous NaOH to adjust the pH to 7-8. The resulting yellow solid was collected by filtration, suspended in saturated aq. NaHCO$_3$, stirred for 1 h, and filtered to give a light green solid. The light green solid was suspended in saturated aqueous NaHCO$_3$, stirred, filtered and washed with saturated aqueous NaHCO$_3$ and water to give an off-white solid. The off-white solid was suspended in water, mixed well, filtered, washed with water, air-dried overnight, and dried under high vacuum at 50° C. to give 8-chloro-3-ethylquinoxalin-2(1H)-one (1 Kg). $^1$H NMR (DMSO-d$_6$) δ ppm 7.69-7.75 (m, 1H), 7.59-7.65 (m, 1H), 7.29 (t, J=8.0 Hz, 1H), 2.84 (q, J=7.4 Hz, 2H), 1.23 (t, J=7.4 Hz, 3H). Mass Spectrum (ESI) m/z=209.1 (M+1).

3,5-dichloro-2-ethylquinoxaline

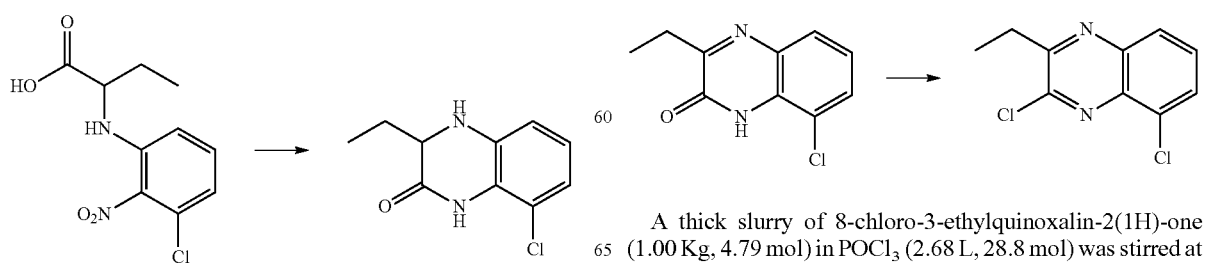

A thick slurry of 8-chloro-3-ethylquinoxalin-2(1H)-one (1.00 Kg, 4.79 mol) in POCl$_3$ (2.68 L, 28.8 mol) was stirred at 100° C. for 2 h. At this time LC-MS analysis showed that the reaction was complete. After the removal of most of the POCl₃ under reduced pressure, the residue was poured carefully into ice-water and neutralized with a combination of 2M aq. NaOH and saturated aq. NaHCO₃. The resulting suspension was extracted with DCM (3×4 L). The organic phase was washed with brine, dried over anhydrous Na₂SO₄, filtered, and evaporated under reduced pressure. The crude was purified by flash column chromatography eluting with hexane/EtOAc (30/1) to give 3,5-dichloro-2-ethylquinoxaline (840 g) as a white solid. ¹H NMR (DMSO-d₆) δ ppm 8.01-8.08 (m, 2H), 7.84 (t, J=8.0 Hz, 1H), 3.10-3.17 (d, J=7.3 Hz, 2H), 1.36 (t, J=7.3 Hz, 3H). Mass Spectrum (ESI) m/z=227.1 (M+1).

2-(1-bromoethyl)-3,5-dichloroquinoxaline

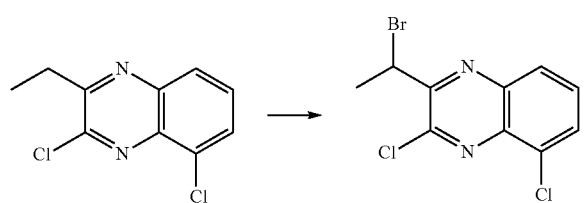

3,5-Dichloro-2-ethylquinoxaline (1.10 Kg, 4.84 mol) was dissolved in CCl₄ (4.4 L) at rt. 1,3-dibromo-5,5-dimethylhydantoin (762 g, 2.66 mol) and benzoyl peroxide (116 g, 0.48 mol) were then added. The resulting suspension was heated at reflux for 2 h. At this time LC-MS analysis showed that the reaction was complete. After cooling to rt white crystals formed in the reaction vessel. The white crystals were collected by filtration, washed with saturated aqueous NaHCO₃ (3×5 L), and dried under high vacuum to give 2-(1-bromoethyl)-3,5-dichloroquinoxaline as a white solid (1.05 Kg). ¹H NMR (DMSO-d₆) δ ppm 8.04-8.12 (m, 2H), 7.78-7.90 (m, 1H), 5.76-5.84 (m, 1H), 2.09 (d, J=6.7 Hz, 3H). Mass Spectrum (ESI) m/z=304.8 [(M+1) (⁷⁹Br)], 306.9 [(M+1) (⁸¹Br)].

2-(1-(3,5-dichloroquinoxalin-2-yl)ethyl)isoindoline-1,3-dione

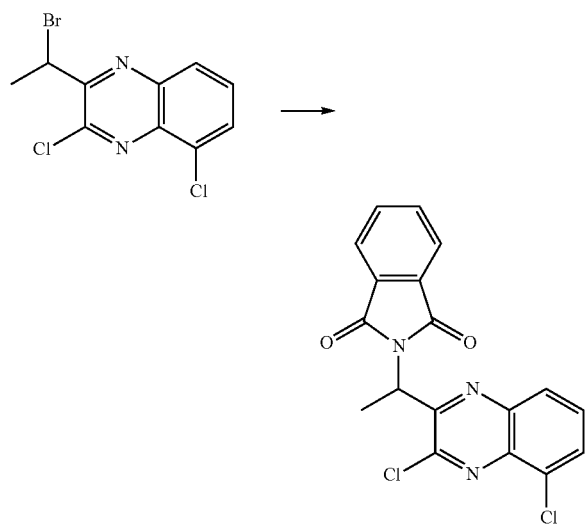

To a solution of 2-(1-bromoethyl)-3,5-dichloroquinoxaline (1.00 Kg, 3.27 mol) in DMF (8.2 L) was added potassium phthalimide (1.21 Kg, 6.54 mol). The reaction mixture was stirred for 3 h. At this time LC-MS analysis showed that the reaction was complete. The mixture was transferred to a 50 L separatory funnel and water (12 L) and EtOAc (6 L) were added to it with stirring. A large amount of white solid crashed out and was collected by filtration. The aqueous. phase was separated and extracted again with EtOAc (2×4 L). The combined organic layers were washed with brine, dried over anhydrous Na₂SO₄, filtered, and the volume was reduced to 5 L under reduced pressure. After cooling to rt, the product was obtained as a white solid. The white solid was filtered, triturated with hexane and dried under vacuum to give 2-(1-(3,5-dichloroquinoxalin-2-yl)ethyl)isoindoline-1,3-dione (1.24 Kg). ¹H NMR (DMSO-d₆) δ ppm 8.02-8.21 (2H, m), 7.83-8.02 (m, 5H), 5.89 (q, J=6.8 Hz, 1H), 1.87 (d, J=6.8 Hz, 3H). Mass Spectrum (ESI) m/z=372.0 (M+1).

(S)-2-(1-(3,5-dichloroquinoxalin-2-yl)ethyl)isoindoline-1,3-dione

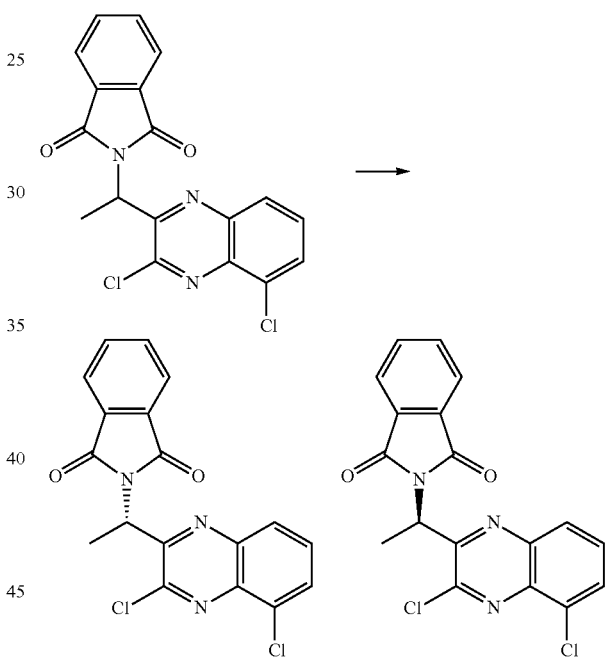

Racemic 2-(1-(3,5-dichloroquinoxalin-2-yl)ethyl)isoindoline-1,3-dione (1 Kg) was purified on a Novasep HPLC unit. The operating conditions used for the separation process were:

Column. CHIRALPAK®AS 20 μM, 11 cm id×25 cm L
Mobile Phase Hexane-IPA 70-30
Flow rate: 400 mL/min
Temperature: 25° C.
UV detection: 340 nm Solubility was 1 g/L in the mobile phase. Stirring and heating were required to keep the sample in solution. The solution was filtered before use. Injection volume was 510 mL every 8.0 minutes. The fractions collected from the chromatographic process were evaporated using Artisan thin-film evaporators and rotary evaporators at 45° C. After solvent removal, the product was dried to constant weight in vacuum oven at 40° C. to give: (S)-2-(1-(3,5-dichloro-quinoxalin-2-yl)ethyl)isoindoline-1,3-dione, 1ˢᵗ enantiomer (425.7 g, 85.1% yield, 98.7% e.e.) and (R)-2-(1-(3,5-dichloroquinoxalin-2-yl)ethyl)isoindoline-1,3-dione, 2<sup>nd</sup> enantiomer (432.5 g, 86.2% yield, 97.7% e.e.).

2-((1S)-1-(5-chloro-3-(2-(methylthio)phenyl)quinoxalin-2-yl)ethyl)isoindoline-1,3-dione

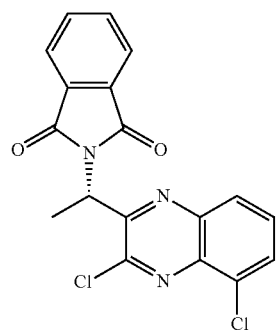

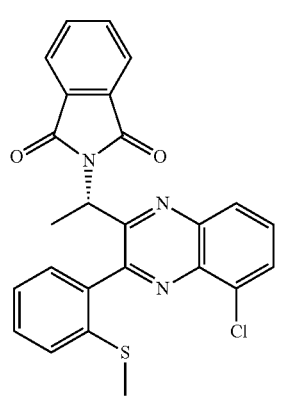

A 5 L three-necked round-bottomed flask equipped with a mechanical stirrer, a condenser, a nitrogen gas inlet and a temperature probe was charged with DMF (2.16 L), (S)-2-(1-(3,5-dichloroquinoxalin-2-yl)ethyl)isoindoline-1,3-dione (273 g, 733 mmol) and 2-(methylthio)phenylboronic acid (136 g, 807 mmol). To the mixture, was added potassium carbonate (203 g, 147 mmol) and [1,1-bis(di-phenylphosphino)ferrocene]palladium(ii) chloride, complex with DCM (29.9 g, 36.7 mmol). The mixture was vacuum purged with $N_2$ (2×), and heated to 100° C. The reaction was monitored by LC-MS, and deemed complete after 4 h. The reaction was cooled to rt (21° C.), and then divided into two batches. Each batch was partitioned between EtOAc (1.08 L) and water (1.35 L) in a 4 L separatory funnel After phase separation, the organic layer was washed with brine (2×500 mL) and concentrated to afford the crude product. The combined batches of crude material were loaded on silica gel and purified by flash chromatography (ISCO/RediSep™) (hexane:EtOAc=10:0 to 6:4) to provide the product as a light brown solid 320 g with 98% LC purity and 95% yield.

$^1$H NMR (400 MHz, DMSO-$d_6$) δ ppm 8.15-8.31 (m, 1H), 8.07 (m, 1H), 7.93 (m, 1H), 7.77 (m, 2H), 7.64 (br.s., 2H), 7.16-7.55 (m, 3H), 6.58-7.02 (m, 1H), 5.72-5.98 (m, 1H), 3.29 (s, 3H), 1.79 (d, J=6.9 Hz, 3H) Mass Spectrum (ESI) m/z=460.0 (M+1).

2-((1S)-1-(5-chloro-3-(2-(methylsulfonyl)phenyl)quinoxalin-2-yl)ethyl)-isoindoline-1,3-dione

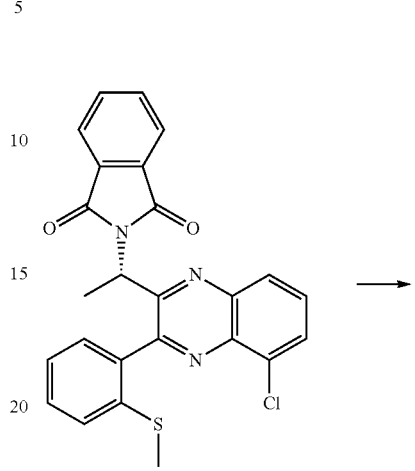

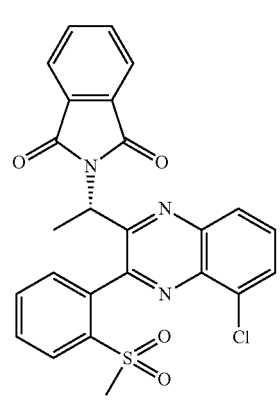

A 5 L three-necked round-bottomed flask equipped with an addition funnel, nitrogen inlet, overhead stirrer and thermocouple was charged with Montmorillonite K10 (274 g, 274 mmol) and water (54.2 mL). The mixture was vigorously stirred for ~10 min, when a free flowing powder was obtained. At this time DCM (1.26 mL) was added followed by Oxone (421 g, 685 mmol). The reaction temperature dropped to 15° C. A solution of 2-((1S)-1-(5-chloro-3-(2-(methylthio)phenyl)quinoxalin-2-yl)ethyl)isoindoline-1,3-dione (126 g, 274 mmol) in DCM (630 mL) was added at rt (18-20° C.) to the montmorillo-nite/oxone suspension through an addition funnel and the internal temperature was controlled below 21° C. by a water/ice bath. The reaction was stirred at rt (19-21° C.) and monitored by LC. It was deemed completion after 96 h. The reaction mixture was filtered and the solids were washed with DCM (2×250 mL). The combined organic solution was washed with 10 wt % aq. solution of $Na_2SO_3$ (2×250 mL), concentrated and dried to afford the product as a light yellow solid 110 g with 97.6% LC purity and 82% yield. $^1$H NMR (400 MHz, DMSO-$d_6$) δ ppm 8.14-8.29 (m, 1H), 7.64-8.14 (m, 8H), 7.52 (dd, J=5.5, 3.0 Hz, 1H), 7.21-7.38 (m, 1H), 5.59-5.94 (m, 1H), 3.10-3.27 (m, 3H), 1.66-1.91 (m, 3H) Mass Spectrum (ESI) m/z=492.0 (M+1).

(S)-1-(5-chloro-3-(2-(methylsulfonyl)phenyl)qui-noxalin-2-yl)ethanamine

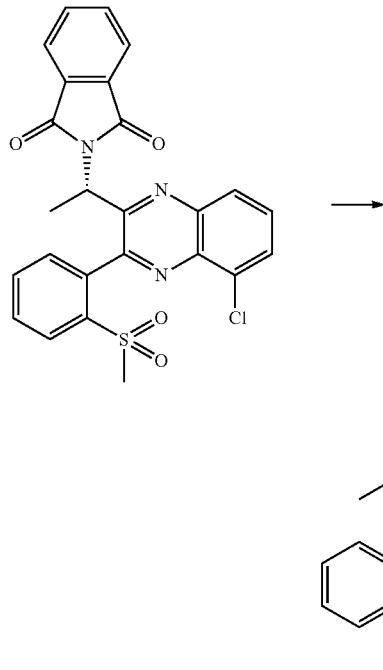

A 5 L three-neck round bottom flask equipped with an overhead stirrer, thermocouple and reflux condenser with a nitrogen inlet was charged with (S)-2-(1-(5-chloro-3-(2-(methylsulfonyl)phenyl)quinoxalin-2-yl)ethyl)isoindoline-1,3-dione (193 g, 392 mmol), water (1351 mL) and hydrazine, 35 wt. % solution in water (711 mL, 785 mmol). The resulting white slurry was vigorously stirred at 65° C. under nitrogen for 6 h and then it was allowed to cool to rt overnight. After this time LC-MS analysis showed complete conversion to the desired product. The white solid was isolated by filtration, washed with water and dried on the glass filter under a stream of nitrogen for 4 h to give (S)-1-(5-chloro-3-(2-(methylsulfonyl)phenyl)quinoxalin-2-yl)ethanamine (129.7 g). Mass Spectrum (ESI) m/z=362.0 (M+1).

(S)-4-amino-6-((1-(5-chloro-3-(2-(methylsulfonyl)phenyl)quinoxalin-2-yl)-ethyl)amino)pyrimidine-5-carbonitrile

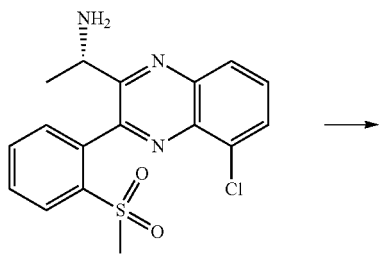

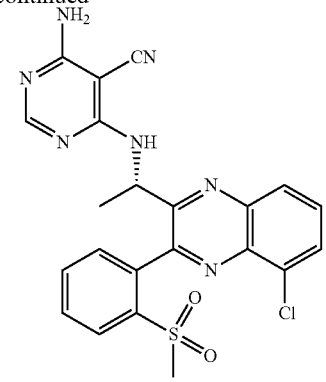

A 3 L three-necked round bottom flask equipped with an overhead stirrer, nitrogen inlet and thermocouple was charged with (1S)-1-(5-chloro-3-(2-(methylsulfonyl)phenyl)quinoxalin-2-yl)ethanamine (130 g, 358 mmol), 4-amino-6-chloropyrimidine-5-carbonitrile (55.4 g, 358 mmol), butan-1-ol (920 mL) and N,N-diisopropylethylamine (187 mL, 1.08 mol). The reaction mixture was heated to an internal temperature of 95-100° C. for 6 h and then allowed to cool to rt overnight. After this time the reaction was heated to an internal temperature of 100° C. and then cooled to an internal temperature of 50° C. Ethyl acetate (~1.5 L) was added at 50° C. and the reaction was allowed to cool to rt. The resulting solution was washed with water (3×1 L), 10 wt % aq. NaHSO$_4$ (4×1 L) and brine (1×500 mL). The separated organic layer was dried over MgSO$_4$, filtered and concentrated in vacuo. The resulting residue was suspended in toluene (1 L), evaporated in vacuo and dried under high vacuum for 36 h (247 g of crude material was obtained). The crude material was suspended in EtOAc (2 L), filtered and washed with a 10 wt % aqueous NaHSO$_4$ solution (4×1 L). A white solid started to form in the EtOAc layer. A magnetic stir bar was added and the suspension was stirred at rt overnight and at 0° C. for 2 h. The white solid was isolated by filtration of the EtOAc and dried on a glass filter under a stream of nitrogen for two days, the EtOAc filtrate (filtrate A) was set aside. The white solid (51 g) was then suspended in EtOAc (2 L) and saturated aqueous NaHCO$_3$ was added (1 L). The resulting suspension was stirred for 15 min resulting in a two layer mixture. The organic layer was separated, dried over MgSO$_4$, filtered concentrated in vacuo to give the desired product. Filtrate A was then concentrated in vacuo, adsorbed on silica and purified by MPLC (DCM/MeOH+10% NH$_4$OH: 100/0 to 90/10) to give 92 g of desired product. The two isolated products were combined and dissolved in EtOH (500 mL). The resulting solution was concentrated in vacuo. This process of dissolution in EtOH and concentration was repeated three times (3×500 mL). The resulting solid was ground (mortar and pestle) to a powder and dried in a vacuum oven (temperature: 90-100° C.) over P$_2$O$_5$ for 84 h. After this time the material was again ground, transferred to an oversized pan and dried under high vacuum at 100-110° C. for 24 h to give (S)-4-amino-6-((1-(5-chloro-3-(2-(methylsulfonyl)phenyl)quinoxalin-2-yl)ethyl)amino)pyrimidine-5-carbonitrile (127.9 g). $^1$H NMR (DMSO-d$_6$) δ ppm 8.06-8.20 (m, 3H), 7.96-7.77 (m, 5H), 7.64-7.65 and 6.79-6.80 (m, 1H), 7.28 (br.s., 2H), 5.42-5.45 (m, 1H), 3.32 and 3.22 (s, 3H), 1.51 and 1.40 (d, J=6.6 Hz, 3H). Mass Spectrum (ESI) m/z=480.0 (M+1). Karl Fisher and GC analysis of an analytical sample showed that the material contained 0.45 wt % of water and 0.55 wt % of EtOH.

Example 6

Preparation of 2-((S)-1-(6-amino-5-cyanopyrimidin-4-ylamino)-ethyl)-3-(2-(methylsulfonyl)phenyl)quinoxaline-5-carbonitrile 2-((S)-1-(1,3-dioxoisoindolin-2-yl)ethyl)-3-(2-(methylsulfonyl)phenyl)-quinoxaline-5-carbonitrile

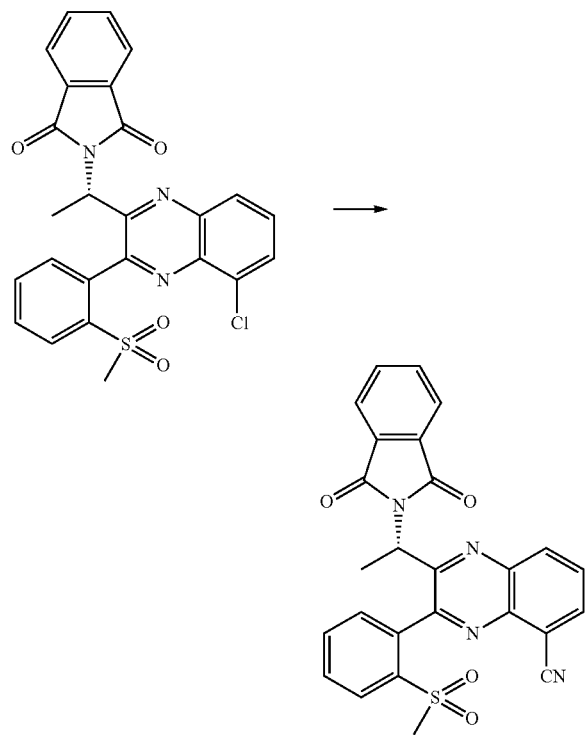

A 5 L three-necked round-bottomed flask equipped with a condenser, nitrogen inlet, overhead stirrer and thermocouple was charged with 2-((1S)-1-(5-chloro-3-(2-(methylsulfonyl)phenyl)quinoxalin-2-yl)ethyl)isoindoline-1,3-dione (400 g, 813 mmol), dicyanozinc (143 g, 1.22 mol) and 1,4-dioxane (4.0 L). The solution was stirred vigorously and degassed with Ar for 1 h. To the solution was then added XPhos pre-catalyst (66.1 g, 89 mmol). The mixture was then degassed with Ar for 1 h and heated to 90° C. The reaction was monitored by LC, and deemed complete after 8 h. The reaction was cooled to rt (20-21° C.) and divided into two batches. For each batch, EtOAc (2.0 L), NaHCO₃ (400 mL) and water (400 mL) were added. The mixture was stirred for 10 min and a precipitate formed. The precipitates were filtered to afford the pure product as a white solid 201.5 g. The mother liquor was washed with brine (800 mL) and the organic layer concentrated to afford the crude product ~400 g. The crude material was then slurried in EtOAc (1.2 L) for 30 min at rt. The solid was filtered, washed with EtOAc (2×400 mL) and dried to afford the product as a tan solid 220 g. All the solids were combined, dried on a glass frit under mild vacuum and a stream of N₂ for 2 days to afford the product as white solid 378 g with 99.6% LC purity and 96% yield. ¹H NMR (400 MHz, DMSO-d₆) δ ppm 8.47-8.68 (m, 2H), 7.66-8.19 (m, 7H), 7.52 (dd, J=5.5, 3.0 Hz, 1H), 7.22-7.40 (m, 1H), 5.61-5.95 (m, 1H), 3.11-3.27 (m, 3H), 1.68-1.93 (m, 3H) Mass Spectrum (ESI) m/z=483.0 (M+1).

2-((S)-1-aminoethyl)-3-(2-(methylsulfonyl)phenyl)quinoxaline-5-carbonitrile

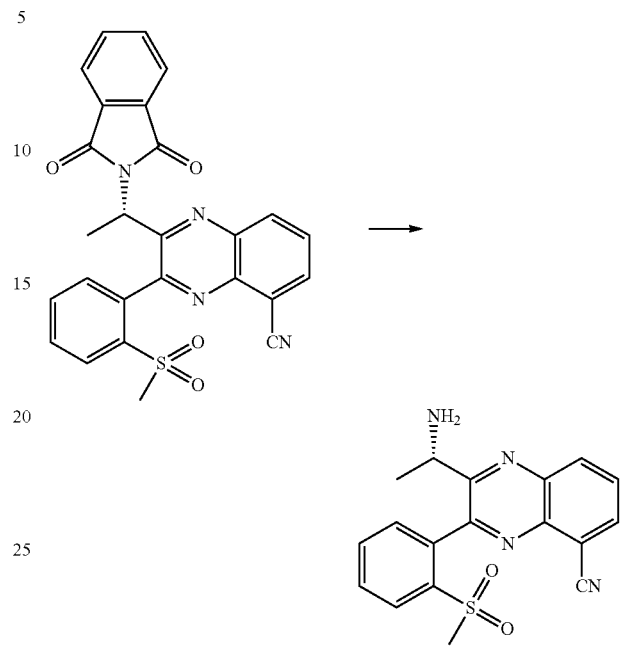

A 5 L three-necked round-bottomed flask equipped with a nitrogen inlet, overhead stirrer and thermocouple was charged with hydrazine hydrate (381 mL, 783 mmol) and EtOH (3.0 L). To the solution was then added 2-((S)-1-(1,3-dioxoisoindolin-2-yl)ethyl)-3-(2-(methylsulfonyl)phenyl)quinoxaline-5-carbonitrile (378 g, 783 mmol) in one portion and heated to 80° C. The reaction was monitored by LC, and deemed complete once the reaction again reached 80° C. The reaction was cooled to room temp (20-21° C.), when DCM (3.0 L) and satd. NaHCO₃ solution (600 mL) were added. After phase separation, the organic layer was washed with brine (2×600 mL), concentrated and dried under vacuum and N₂ flow for 24 h to afford the product as a light yellow solid 257.7 g with 94.4% LC purity, (no R enantiomer detected) and 93% yield. ¹H NMR (400 MHz, DMSO-d₆) δ ppm 8.45-8.54 (m, 2H), 8.18 (dt, J=7.7, 1.5 Hz, 1H), 8.05 (dd, J=8.5, 7.4 Hz, 1H), 7.76-8.00 (m, 3H), 3.83-4.03 (m, 1H), 3.25-3.32 (m, 3H), 1.19-1.39 (m, 3H) Mass Spectrum (ESI) m/z=353.0 (M+1).

2-((S)-1-(6-amino-5-cyanopyrimidin-4-ylamino)ethyl)-3-(2-(methylsulfonyl)-phenyl)quinoxaline-5-carbonitrile

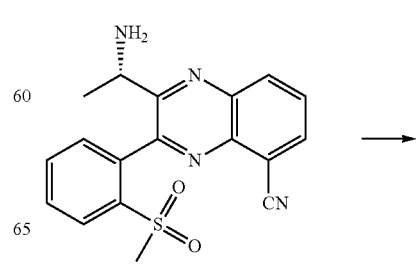

-continued

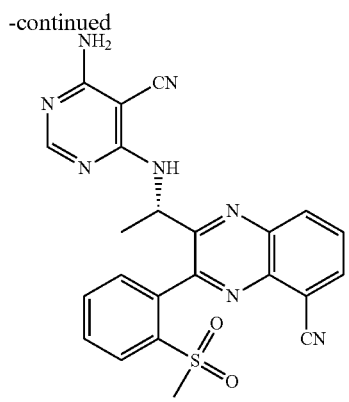

A 5 L three-necked round-bottomed flask equipped with a mechanical stirrer, a condenser, a nitrogen gas inlet and a temperature probe was charged with 2-((S)-1-aminoethyl)-3-(2-(methylsulfonyl)phenyl)quinoxaline-5-carbonitrile (257.7 g, 731 mmol), 4-amino-6-chloropyrimidine-5-carbonitrile (120 g, 775 mmol), and butan-1-ol (2.5 L). The solution was stirred at rt (19-22° C.) for 5 min and N,N-diisopropylethylamine (363 mL, 219 mmol) was added in one portion. The solution was heated to 95° C., monitored by LC, and deemed complete after 4 h. The reaction was cooled to rt when EtOAc (2.0 L) and water (500 mL) were added. The two layers was separated and the organic layer was washed with brine (500 mL), concentrated until most of the EtOAc was removed, and a precipitate formed. The precipitate was filtered and washed with a minimum amount of MeOH. The solid was dried under vacuum for 18 h to afford a light yellow solid, 305 g. The mother liquor was concentrated, until more product precipitated. The solid was filtered, washed with MeOH (2×200 mL), dried under vacuum for 24 h to afford the product as a solid (45 g). A 5 L three-necked round-bottomed flask equipped with a mechanical stirrer, a nitrogen gas inlet and a temperature probe was charged with the combined 350 g crude product and MeOH (3.5 L). The mixture was stirred at rt (19-22° C.) for 2 days. The solid was filtered, washed with MeOH (2×350 mL), dried under vacuum and N$_2$ flow for 24 h to afford a cream colored solid (276.2 g) with 99.4% HPLC purity, (no R-enantiomer detected) and 80% yield. $^1$H NMR (400 MHz, DMSO-d$_6$) δ ppm 8.43-8.59 (m, 2H), 8.01-8.23 (m, 2H), 7.71-7.99 (m, 4H), 7.61 (d, J=7.0 Hz, 1H), 7.24 (br. s., 2H), 5.33-5.68 (m, 1H), 3.19-3.33 (m, 3H), 1.34-1.55 (m, 3H) Mass Spectrum (ESI) m/z=471.1 (M+1).

Example 7

Preparation of (S)-4-amino-6-(1-(6-fluoro-3-(pyridine-2-yl)-quinoxalin-2-yl)ethyl)amino)pyrimidine-5-carbonitrile 2-((4-fluoro-2-nitrophenyl)amino)butanoic acid

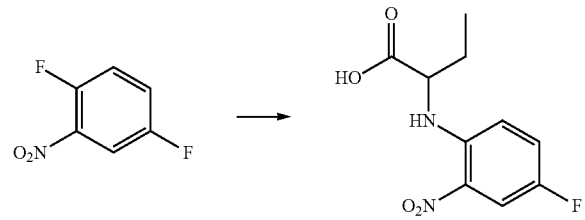 [SMILES: O=[N+]([O-])c1cc(F)ccc1F ; CCC(Nc1ccc(F)cc1[N+](=O)[O-])C(=O)O]

A mixture of 2,5-difluoronitrobenzene (119 ml, 1.10 mol), 2-aminobutanoic acid (114 g, 1.10 mol), and potassium carbonate (152.2 g, 1.10 mol) in dimethyl sulfoxide (410 ml, 1.10 mol) was stirred at 80° C. for 23 h. ([Note 1]: The mixture had a deep orange red color. The internal temperature of the mixture went up to ~110° C. for 1 h and then went down to 80° C.). After 23 h, the reaction was cooled to rt and carefully poured into water (2 L+1 L). The aqueous mixture was washed with diethyl ether (1 L×2) to remove organic impurities. The aqueous layer was then acidified to ~pH 1.5 with concentrated HCl (300 mL) to generate a yellow solid. The yellow solid was collected by filtration, washed with water (3 L), and air-dried to give the desired product, a wet orange solid. The wet orange solid was recrystallized from 3 L toluene and stood at rt overnight to afford the desired product as an orange crystalline solid. The orange crystalline solid was filtered, washed with toluene (2 L), and dried under high vacuum at 80° C. for 4 h and then on lyophilizer overnight to afford 2-(4-fluoro-2-nitrophenylamino)-butanoic acid (203.6 g, 76.4% yield) as an orange crystalline solid. The orange crystalline solid was carried on without further purification to the next step.
$^1$H NMR (400 MHz, DMSO-d$_6$) δ ppm 13.30 (br. s. 1H), 8.28 (d, J=7.4 Hz, 1H), 7.90 (dd, J=9.4, 2.9 Hz, 1H), 7.49-7.60 (m, 1H), 7.09 (dd, J=9.6, 4.7 Hz, 1H), 4.49 (dt, J=7.2, 5.5 Hz, 1H), 1.79-2.00 (m, 2H), 0.85-0.93 (m, 3H), Mass Spectrum (ESI) m/e=243.1 (M+1).

3-Ethyl-7-fluoro-3,4-dihydroquinoxalin-2(1H)-one

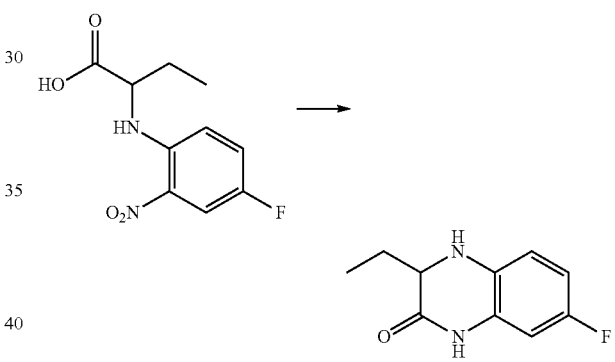

The heterogeneous mixture of 2-(4-fluoro-2-nitrophenylamino)butanoic acid (181.7 g, 750.0 mmol), 3 N aq. HCl (750.0 ml, 2250 mmol), and ethanol (1923 ml, 750.0 mmol) in 5-L three neck round bottom flask was added Tin(II) chloride dihydrate (507.7 g, 2250 mmol) and the organe mixture was heated at 78° C. with stirring using an overhead stirrer for 4 h ([Note 1]: The orange heterogeneous mixture became an orange homogeneous mixture and the orange color changed to a red color over ~2 hour). After 4 h, the mixture was cooled to rt and concentrated under reduced pressure to remove ethanol, and left at rt for 48 h. The resulting yellow precipitate was collected by filtration and washed with water (500 mL). The yellow solid was suspended in ice water (1 L) and the mixture was adjusted ~pH 13 with KOH (~250 g). The heterogeneous mixture was extracted with DCM (1 L×3). The combined organic layers were washed with water (1 L×1) and brine (1 L×1), dried over Na$_2$SO$_4$, filtered, and concentrated under reduced pressure to give 3-ethyl-7-fluoro-3,4-dihydroquinoxalin-2(1H)-one (60.92 g, 41.8% yield) as a light yellow solid. $^1$H NMR (400 MHz, DMSO-d$_6$) δ ppm 10.26 (s, 1H), 6.68 (dd, J=8.6, 5.5 Hz, 1H), 6.47-6.61 (m, 2H), 5.95 (d, J=1.2 Hz, 1H), 3.62 (ddd, J=6.7, 5.0, 2.0 Hz, 1H), 1.50-1.72 (m, 2H), 0.92 (t, J=7.4 Hz, 3H), Mass Spectrum (ESI) m/e=195.1 (M+1).

3-Ethyl-7-fluoroquinoxalin-2(1H)-one

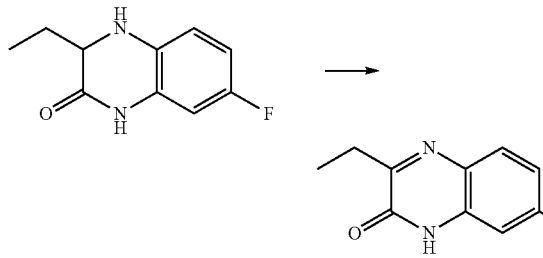

To a homogeneous solution of 3-ethyl-7-fluoro-3,4-dihydroquinoxalin-2(1H)-one (60.61 g, 312.1 mmol) and 1,4-dioxane (1350 ml) was added 2,3-dichloro-5,6-dicyano-1,4-benzoquinone (75.91 g, 327.7 mmol) and the mixture was stirred using an overhead stirrer at rt for 2.5 h. At this time, the mixture was concentrated under reduced pressure to give a brown residue. The brown residue was suspended in saturated aqueous $NaHCO_3$ (2 L), stirred for 30 min, filtered, washed with saturated aqueous $NaHCO_3$ (1 L) to give a light green solid. The light green solid was re-suspended in saturated aqueous $NaHCO_3$ (500 mL), well mixed, filtered, and washed with saturated aqueous $NaHCO_3$ (500 mL) to give an off-white solid. The off-white solid was suspended in water (500 mL), well mixed, filtered, washed with water (1 L), air-dried overnight, and dried under high vacuum at 22° C. for 2 h to give 3-ethyl-7-fluoroquinoxalin-2(1H)-one (56.87 g, 94.8% yield) as an off-white solid. $^1$H NMR (400 MHz, DMSO-$d_6$) δ ppm 12.36 (br. S, 1H), 7.76 (dd, J=9.0, 5.9 Hz, 1H), 7.11 (td, J=8.8, 2.7 Hz, 1H), 7.00 (dd, J=9.6, 2.7 Hz, 1H), 2.78 (q, J=7.4 Hz, 2H), 1.20 (t, J=7.4 Hz, 3H) Mass Spectrum (ESI) m/e=193.0 (M+1).

3-(1-Bromoethyl)-7-fluoroquinoxalin-2(1H)-one

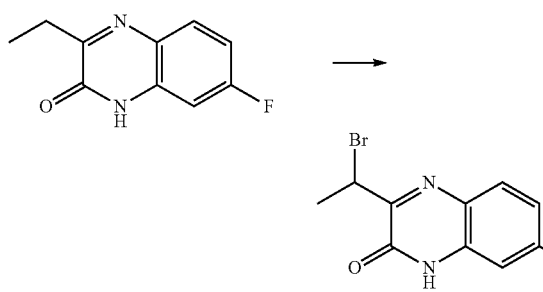

3-Ethyl-7-fluoroquinoxalin-2(1H)-one (20.61 g, 107.2 mmol) and 1,3-dibromo-5,5-dimethylhydantoin (18.77 g, 64.34 mmol) suspended in carbon tetrachloride (1072 ml, 107.2 mmol). To the heterogeneous mixture was added benzoyl peroxide (3.463 g, 10.72 mmol) and the mixture was heated at reflux with stirring (oil bath temperature: 80° C.) for 20 h. After 20 h, the mixture was cooled to rt. After cooling, the mixture was poured into saturated aqueous sodium bicarbonate solution (1 L) with stirring. The precipitate was collected by filtration and washed with water (1 L) to give 3-(1-bromoethyl)-7-fluoroquinoxalin-2(1H)-one (23.19 g, 79.8% yield) as a tan solid:

$^1$H NMR (400 MHz, DMSO-$d_6$) δ ppm 12.68 (br. S, 1H), 7.85 (dd, J=9.0, 5.9 Hz, 1H), 7.19 (td, J=8.8, 2.7 Hz, 1H), 7.05 (dd, J=9.8, 2.7 Hz, 1H), 5.62 (q, J=6.7 Hz, 1H), 1.99 (d, J=6.7 Hz, 3H), ~90% pure Mass Spectrum (ESI) m/e=271.0 [M+H ($^{79}$Br)]$^+$ and 273.0 [M+H ($^{81}$Br)]$^+$

2-(1-Bromoethyl)-3-chloro-6-fluoroquinoxaline

3-Chloro-2-(1-chloroethyl)-6-fluoroquinoxaline

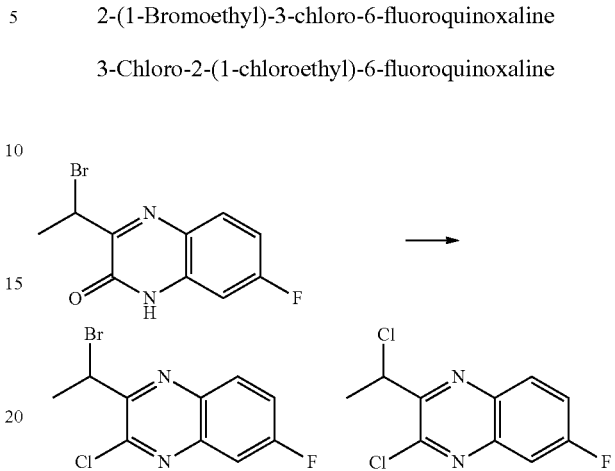

A heterogeneous mixture of 3-(1-bromoethyl)-7-fluoroquinoxalin-2(1H)-one (58.86 g, 217.1 mmol) and phosphorous oxychloride (198.8 ml, 2171 mmol) in a 1 L round bottom flask was stirred at 100° C. for 2 h. The mixture was hetereogeneous in the beginning of the reaction and then homogenesous black solution over 1 h. After 2 h, the mixture was cooled to rt and concentrated under reduced pressure. To the black residue was carefully added ice (~400 ml) in portions and then water (200 ml) with stirring. The mixture was neutralized with $NH_4OH$ (200 ml) and ice (~200 ml) with stirring. The resulting precipitate was collected by filtration, rinsed with water (1 L), and dried under high vacuum overnight to give 2-(1-bromoethyl)-3-chloro-6-fluoroquinoxaline (58.31 g, 92.8% yield) including 3-chloro-2-(1-chloroethyl)-6-fluoroquinoxaline as a brown solid.

$^1$H NMR (400 MHz, DMSO-$d_6$), ratio of bromoethyl analog and chloroethyl analog=2.5:1 Mass Spectrum (ESI) m/e=288.9 [M+H($^{79}$Br)]$^+$ and 291.0 [M+H ($^{81}$Br)]$^+$

2-(1-(3-Chloro-6-fluoroquinoxalin-2-yl)ethyl)isoindoline-1,3-dione

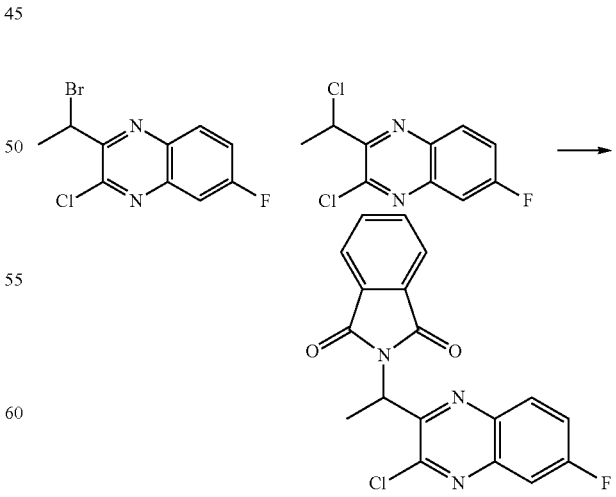

To a mixture of 2-(1-bromoethyl)-3-chloro-6-fluoroquinoxaline (57.17 g, 197.5 mmol) containing 3-chloro-2-(1-chloroethyl)-6-fluoroquinoxaline (48.39 g, 197.5 mmol) in N,N-dimethylformamide (700.0 ml, 197.5 mmol) was added potassium phthalimide (91.43 g, 493.6 mmol) at rt and the mixture was stirred at rt for 1 h. After 1 h, to the mixture was added water (2 L). The mixture was extracted with DCM (500 mL×3). The combined organic layers were washed with brine (1 L×1), dried over MgSO$_4$, filtered, and concentrated under reduced pressure to give a red liquid. The red liquid was filtered though a plug of silica (5.5 inch diameter×5 inch height), and eluented with 20% of EtOAc in hexane, then 30% of EtOAc in hexane, and then 100% of EtOAc as eluent to give two fractions. Second fraction, desired product 2-(1-(3-chloro-6-fluoroquinoxalin-2-yl)ethyl)isoindoline-1,3-dione (53.367 g, 75.97% yield) as a pink solid. $^1$H NMR (400 MHz, DMSO-d$_6$) δ ppm 8.25 (dd, J=9.4, 5.9 Hz, 1H), 7.81-7.95 (m, 6H), 5.86 (q, J=6.8 Hz, 1H), 1.86 (d, J=7.0 Hz, 3H). Mass Spectrum (ESI) m/e=356.0 (M+1).

2-(1-(6-Fluoro-3-(pyridin-2-yl)quinoxalin-2-yl)ethyl)isoindoline-1,3-dione

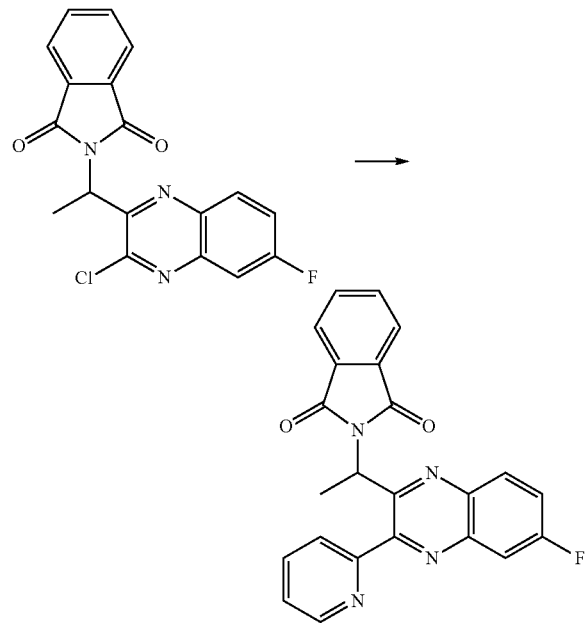

A solution of 2-(1-(3-chloro-6-fluoroquinoxalin-2-yl)ethyl)isoindoline-1,3-dione (50.14 g, 140.9 mmol), 2-tri-n-butylstannylpyridine (80% pure) (76.95 ml, 211.4 mmol), and tetrakis(triphenylphosphine)palladium(0) (16.29 g, 14.09 mmol) in 1,4-dioxane (1175 ml, 140.9 mmol) was stirred at 110° C. for 29 h. After 29 h, the mixture was cooled to rt and concentrated under reduced pressure to give a green syrupy solid. To the residue was added DCM (200 mL). The mixture was heated under reflux for 20 min and then cooled to 0° C. with stirring. The solid was collected by filtration and washed with EtOAc-hexane (1:5, 500 mL) to give the desired product (52.82 g, 94.07% yield). The dark brown solid was dissolved in CH$_2$Cl$_2$:MeOH (9:1, 400 mL, warm), filtered through a plug of silica gel (150 g, 8.5 cm diameter×5.5 cm height) to remove residual palladium and washed with CH$_2$Cl$_2$:MeOH (9:1, 600 mL). The filtrate was concentrated under reduced pressure to give a brown solid (49.94 g, 88.9% yield). The brown solid was suspended in EtOAc-hexane (1:9, 400 mL) and the mixture was heated under reflux for 40 min. The mixture was cooled to rt, filtered, washed with EtOAc-hexane (1:9, 600 mL), and dried to give the desired product 2-(1-(6-fluoro-3-(pyridin-2-yl)quinoxalin-2-yl)ethyl)isoindoline-1,3-dione (47.76 g, 85.06% yield) as a tan solid. $^1$H NMR (400 MHz, DMSO-d$_6$) δ ppm 8.47-8.53 (m, 1H), 8.20 (dd, J=9.4, 5.9 Hz, 1H), 7.94 (dd, J=9.4, 2.7 Hz, 1H), 7.85 (td, J=8.9, 2.9 Hz, 1H), 7.64-7.80 (m, 6H), 7.30-7.37 (m, 1H), 6.42 (q, J=6.9 Hz, 1H), 1.76 (d, J=7.0 Hz, 3H). Mass Spectrum (ESI) m/e=399.1 (M+1).

1-(6-fluoro-3-(pyridin-2-yl)quinoxalin-2-yl)ethanamine

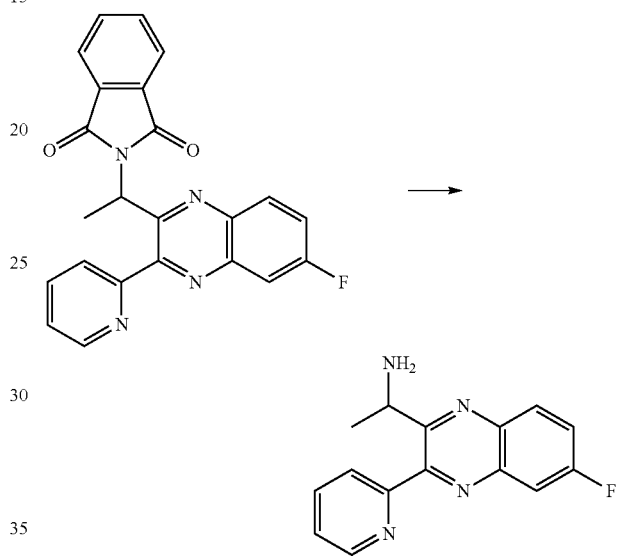

To a heterogeneous mixture of 2-(1-(6-fluoro-3-(pyridin-2-yl)quinoxalin-2-yl)ethyl)isoindoline-1,3-dione (47.26 g, 118.6 mmol) in ethanol (768.3 ml, 118.6 mmol) was added hydrazine, monohydrate (28.77 ml, 593.1 mmol) and the mixture was stirred at 95° C. for 1 h. The hetereogeneous reaction mixture went into solution after 15 min, but voluminous white ppt followed. After 1 h the mixture was cooled to rt. The precipitate was broken up with a spatula, filtered and washed with EtOAc (3×250 mL portions). The filtrate was concentrated under reduced pressure. The residue was redissolved in EtOAc (600 mL) and water (300 mL). The organic layer was separated and the aqueous layer was extracted with EtOAc (100 mL×3). The combined organic layer were dried over MgSO$_4$, filtered, and concentrated under reduced pressure to give 1-(6-fluoro-3-(pyridin-2-yl)quinoxalin-2-yl)ethanamine (30.95 g, 97.25% yield) as a brown solid. $^1$H NMR (400 MHz, DMSO-d$_6$) δ ppm 8.75 (dq, J=4.7, 0.9 Hz, 1H), 8.20 (dd, J=9.0, 5.9 Hz, 1H), 7.98-8.11 (m, 2H), 7.91 (dd, J=9.4, 2.7 Hz, 1H), 7.78-7.86 (m, 1H), 7.56-7.61 (m, 1H), 4.66 (q, J=6.7 Hz, 1H), 2.08 (br. S, 2H), 1.35 (d, J=6.7 Hz, 3H). Mass Spectrum (ESI) m/e=269.0 (M+1). [Chiral HPLC] (Chiralpak AD-H column, 0.46×250 mm, 5 um) using 10% isocratic of isopropanol in hexane as eluent: two peaks at 9.350 min and at 10.678 min at 254 nm, (Chiralpak OD-H column, 0.46×250 mm, 5 um) using 10% isocratic of isopropanol in hexane as eluent: two peaks at 9.69 min and at 11.22 min at 254 nm.

(S)-1-(6-Fluoro-3-(pyridin-2-yl)quinoxalin-2-yl) ethanamine (R)-1-(6-Fluoro-3-(pyridin-2-yl) quinoxalin-2-yl) ethanamine

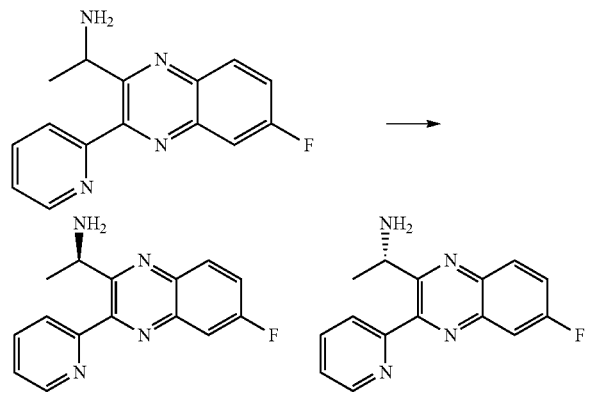

Chiral Separation:

The racemic mixture (30.95 g) was submitted to chiral separation using SFC. Sample was dissolved in 800 mL MeOH(+trace TFA), 1.3 mL sample solution, i.e. 50.3 mg each injection onto separation system. Semi-Prep supercritical fluid chromatography (SFC) was carried out using a Thar 350 SFC (outlet pressure: 117 bar, at 327 nm) with an: AS-H column, 250×30 mm (5 micron) Mobile Phase: 36 g/min MeOH(0.2% DEA) plus 54 g/min $CO_2$ (Temp.=22° C.) After chiral separation, each fraction was co-evaporated two times with toluene and ethanol to remove diethylamine First Peak on AS-H column and second peak on AD-H column (10.678 min): (R)-1-(6-fluoro-3-(pyridin-2-yl)quinoxalin-2-yl)ethanamine (13.5173 g, 50.4 mmol, 43.7% yield) as a brown solid. $^1$H NMR (400 MHz, DMSO-$d_6$) δ ppm 8.76 (dq, J=4.7, 0.9 Hz, 1H), 8.20 (dd, J=9.0, 5.9 Hz, 1H), 7.99-8.10 (m, 2H), 7.91 (dd, J=9.4, 2.7 Hz, 1H), 7.82 (td, J=8.9, 2.9 Hz, 1H), 7.56-7.61 (m, 1H), 4.66 (q, J=6.7 Hz, 1H), 2.07 (s, 2H), 1.35 (d, J=6.7 Hz, 3H), it contained triphenylphosphine oxide; Mass Spectrum (ESI) m/e=269.0 (M+1). [HPLC] a peak at 4.996 min, 99.56% pure at 254 nm; [Chiral HPLC] (Chiralpak AD-H column, 0.46×250 mm, 5 mm) using 10% isocratic of isopropanol in hexane as eluent: a peak at 11.432 min (second-eluting enantiomer) at 254 nm; [Enantiomeric Excess Analysis]: 99% ee, first-eluting enantiomer on AS-H column. Second peak on AS-H column and first peak on AD-H column (9.350 min): (S)-1-(6-fluoro-3-(pyridin-2-yl) quinoxalin-2-yl)ethanamine (12.6738 g, 47.2 mmol, 40.9% yield) as a brown syrupy solid: $^1$H NMR (400 MHz, DMSO-$d_6$) δ ppm 8.73-8.78 (m, J=4.8, 1.2, 0.9, 0.9 Hz, 1H), 8.20 (dd, J=9.4, 5.9 Hz, 1H), 7.99-8.10 (m, 2H), 7.91 (dd, J=9.4, 2.7 Hz, 1H), 7.82 (td, J=8.9, 2.9 Hz, 1H), 7.58 (ddd, J=7.4, 4.9, 1.4 Hz, 1H), 4.66 (q, J=6.4 Hz, 1H), 2.07 (br. s., 2H), 1.35 (d, J=6.7 Hz, 3H); Mass Spectrum (ESI) m/e=269.0 (M+1). [Chiral HPLC] (Chiralpak AD-H column, 0.46×250 mm, 5 mm) using 10% isocratic of isopropanol in hexane as eluent: a peak at 9.135 min (first-eluting enantiomer) at 254 nm; [Enantiomeric Excess Analysis]: 98.86% ee, second-eluting enantiomer on AS-H column. The stereochemistry was confirmed as S-isomer in the next step.

(S)-4-Amino-6-((1-(6-fluoro-3-(pyridin-2-yl)quinoxalin-2-yl)ethyl)amino)-pyrimidine-5-carbonitrile

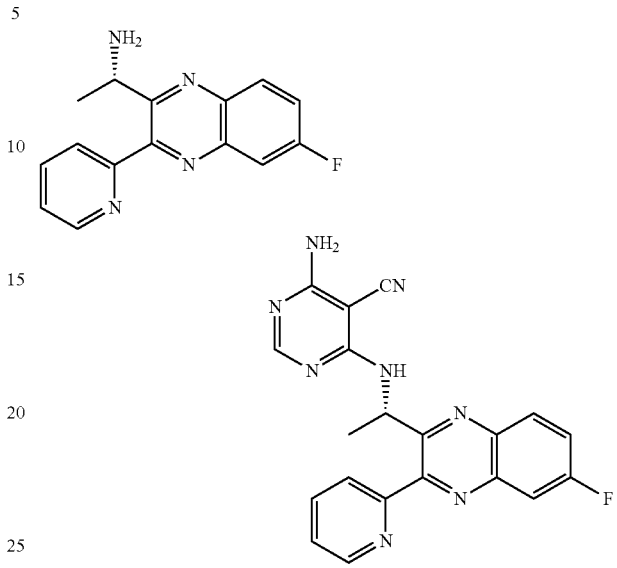

A mixture of 4-amino-6-chloropyrimidine-5-carbonitrile (0.060 g, 0.39 mmol), (S)-1-(6-fluoro-3-(pyridin-2-yl)quinoxalin-2-yl)ethanamine (0.105 g, 0.391 mmol), and N,N-diisopropylethylamine (0.205 mL, 1.17 mmol) in butan-1-ol (3.91 mL) was stirred at 120° C. for 3 h. After 3 h, the mixture was removed from the heat and left at rt. The mixture was concentrated under reduced pressure to give a yellow solid. To the yellow solid was added water (30 mL). The resulting solid was filtered, washed with water (30 mL), and air-dried to give the product as a brown solid. The brown solid was purified by column chromatography on a 40 g of Redi-Sep column using 0 to 50% gradient of $CH_2Cl_2$:MeOH:$NH_4$OH (89:9:1) in $CH_2Cl_2$ over 14 min and then 50% isocratic of $CH_2Cl_2$:MeOH:$NH_4$OH (89:9:1) in $CH_2Cl_2$ for 14 min as eluent to give a light yellow solid (0.1246 g). The light yellow solid was suspended in EtOAc-hexane (1:4), filtered, and dried to give (S)-4-amino-6-(1-(6-fluoro-3-(pyridin-2-yl) quinoxalin-2-yl)ethylamino)pyrimidine-5-carbonitrile (0.1121 g, 0.290 mmol, 74.1% yield) as a tan solid.

$^1$H NMR (400 MHz, DMSO-$d_6$) δ ppm 8.66-8.74 (m, 1H), 8.19 (dd, J=9.4, 5.9 Hz, 1H), 7.99-8.09 (m, 2H), 7.95 (dd, J=9.4, 2.7 Hz, 1H), 7.80-7.89 (m, 2H), 7.70 (d, J=7.4 Hz, 1H), 7.53 (ddd, J=6.9, 5.0, 1.8 Hz, 1H), 7.20 (br. s., 2H), 6.09-6.21 (m, 1H), 1.54 (d, J=6.7 Hz, 3H); Mass Spectrum (ESI) m/e=387.1 (M+1). [Chiral HPLC] (Chiralpak AD-H column, 0.46×250 mm, 5 mm) using 10% isocratic of isopropanol in hexane as eluent: a peak at 16.038 min at 254 nm.

Biological Assays

Recombinant expression of PI3Ks

Full length p110 subunits of PI3k α, β and δ, N-terminally labeled with polyHis tag, were coexpressed with p85 with Baculo virus expression vectors in sf9 insect cells. P110/p85 heterodimers were purified by sequential Ni-NTA, Q-HP, Superdex-100 chromatography. Purified α, β and δ isozymes were stored at −20° C. in 20 mM Tris, pH 8, 0.2M NaCl, 50% glycerol, 5 mM DTT, 2 mM Na cholate. Truncated PI3Kγ, residues 114-1102, N-terminally labeled with polyHis tag, was expressed with Baculo virus in Hi5 insect cells. The γ isozyme was purified by sequential Ni-NTA, Superdex-200, Q-HP chromatography. The γ isozyme was stored frozen at −80° C. in NaH$_2$PO$_4$, pH 8, 0.2M NaCl, 1% ethylene glycol, 2 mM β-mercaptoethanol.

|  | Alpha | Beta | Delta | gamma |
|---|---|---|---|---|
| 50 mM Tris | pH 8 | pH 7.5 | pH 7.5 | pH 8 |
| MgCl2 | 15 mM | 10 mM | 10 mM | 15 mM |
| Na cholate | 2 mM | 1 mM | 0.5 mM | 2 mM |
| DTT | 2 mM | 1 mM | 1 mM | 2 mM |
| ATP | 1 uM | 0.5 uM | 0.5 uM | 1 uM |
| PIP2 | none | 2.5 uM | 2.5 uM | none |
| time | 1 h | 2 h | 2 h | 1 h |
| [Enzyme] | 15 nM | 40 nM | 15 nM | 50 nM |

In Vitro Enzyme Assays.

Assays were performed in 25 µL with the above final concentrations of components in white polyproplyene plates (Costar 3355). Phospatidyl inositol phosphoacceptor, PtdIns (4,5)P2 P4508, was from Echelon Biosciences. The ATPase activity of the alpha and gamma isozymes was not greatly stimulated by PtdIns(4,5)P2 under these conditions and was therefore omitted from the assay of these isozymes. Test compounds were dissolved in dimethyl sulfoxide and diluted with three-fold serial dilutions. The compound in DMSO (1 µL) was added per test well, and the inhibition relative to reactions containing no compound, with and without enzyme was determined After assay incubation at rt, the reaction was stopped and residual ATP determined by addition of an equal volume of a commercial ATP bioluminescence kit (Perkin Elmer EasyLite) according to the manufacturer's instructions, and detected using a AnalystGT luminometer.

Human B Cells Proliferation Stimulate by Anti-IgM

Isolate Human B Cells:

Isolate PBMCs from Leukopac or from human fresh blood. Isolate human B cells by using Miltenyi protocol and B cell isolation kit II.-human B cells were Purified by using AutoMacs.column.

Activation of Human B Cells

Use 96 well Flat bottom plate, plate 50000/well purified B cells in B cell proliferation medium (DMEM+5% FCS, 10 mM Hepes, 50 µM 2-mercaptoethanol); 150 µL medium contain 250 ng/mL CD40L-LZ recombinant protein (Amgen) and 2 µg/mL anti-Human IgM antibody (Jackson ImmunoReseach Lab.#109-006-129), mixed with 50 µL B cell medium containing PI3K inhibitors and incubate 72 h at 37° C. incubator. After 72 h, pulse labeling B cells with 0.5-1 uCi/well $^3$H thymidine for overnight ~18 h, and harvest cell using TOM harvester.

Human B Cells Proliferation Stimulate by IL-4

Isolate Human B Cells:

Isolate human PBMCs from Leukopac or from human fresh blood. Isolate human B cells using Miltenyi protocol—B cell isolation kit. Human B cells were Purified by AutoMacs.column.

Activation of Human B Cells

Use 96-well flat bottom plate, plate 50000/well purified B cells in B cell proliferation medium (DMEM+5% FCS, 50 µM 2-mercaptoethanol, 10 mM Hepes). The medium (150 µL) contain 250 ng/mL CD40L-LZ recombinant protein (Amgen) and 10 ng/mL IL-4 (R&D system #204-IL-025), mixed with 50 150 µL B cell medium containing compounds and incubate 72 h at 37° C. incubator. After 72 h, pulse labeling B cells with 0.5-1 uCi/well 3H thymidine for overnight ~18 h, and harvest cell using TOM harvester.

Specific T Antigen (Tetanus Toxoid) Induced Human PBMC Proliferation Assays

Human PBMC are prepared from frozen stocks or they are purified from fresh human blood using a Ficoll gradient. Use 96 well round-bottom plate and plate 2×10$^5$ PBMC/well with culture medium (RPMI1640+10% FCS, 50 uM 2-Mercaptoethanol, 10 mM Hepes). For IC$_{50}$ determinations, PI3K inhibitors was tested from 10 µM to 0.001 µM, in half log increments and in triplicate. Tetanus toxoid, T cell specific antigen (University of Massachusetts Lab) was added at 1 mg/mL and incubated 6 days at 37° C. incubator. Supernatants are collected after 6 days for IL2 ELISA assay, then cells are pulsed with $^3$H-thymidine for ~18 h to measure proliferation.

GFP Assays for Detecting Inhibition of Class Ia and Class III PI3K

AKT1 (PKBa) is regulated by Class Ia PI3K activated by mitogenic factors (IGF-1, PDGF, insulin, thrombin, NGF, etc.). In response to mitogenic stimuli, AKT1 translocates from the cytosol to the plasma membrane Forkhead (FKHRL1) is a substrate for AKT1. It is cytoplasmic when phosphorylated by AKT (survival/growth). Inhibition of AKT (stasis/apoptosis)-forkhead translocation to the nucleus FYVE domains bind to PI(3)P. the majority is generated by constitutive action of PI3K Class III AKT Membrane Ruffling Assay (CHO-IR-AKT1-EGFP Cells/GE Healthcare)

Wash cells with assay buffer. Treat with compounds in assay buffer 1 h. Add 10 ng/mL insulin. Fix after 10 min at room temp and image Forkhead Translocation Assay (MDA MB468 Forkhead-DiversaGFP Cells)

Treat cells with compound in growth medium 1 h. Fix and image.

Class III PI(3)P assay (U20S EGFP-2XFYVE Cells/GE Healthcare)

Wash cells with assay buffer. Treat with compounds in assay buffer 1 h. Fix and image.

Control for all 3 assays is 1001 Wortmannin:

AKT is cytoplasmic

Forkhead is nuclear

PI(3)P depleted from endosomes

Biomarker Assay: B-Cell Receptor Stimulation of CD69 or B7.2 (CD86) Expression

Heparinized human whole blood was stimulated with 10 µg/mL anti-IgD (Southern Biotech, #9030-01). 90 µL of the stimulated blood was then aliquoted per well of a 96-well plate and treated with 10 µL of various concentrations of blocking compound (from 10-0.0003 µM) diluted in IMDM+ 10% FBS (Gibco). Samples were incubated together for 4 h (for CD69 expression) to 6 h (for B7.2 expression) at 37° C. Treated blood (50 µL) was transferred to a 96-well, deep well plate (Nunc) for antibody staining with 10 µL each of CD45-PerCP (BD Biosciences, #347464), CD19-FITC (BD Biosciences, #340719), and CD69-PE (BD Biosciences, #341652). The second 50 µL of the treated blood was transferred to a second 96-well, deep well plate for antibody staining with 10 µL each of CD19-FITC (BD Biosciences, #340719) and CD86-PeCyS (BD Biosciences, #555666). All stains were performed for 15-30 min in the dark at rt. The blood was then lysed and fixed using 450 µL of FACS lysing solution (BD Biosciences, #349202) for 15 min at rt. Samples were then washed 2× in PBS+2% FBS before FACS analysis. Samples were gated on either CD45/CD19 double positive cells for CD69 staining, or CD19 positive cells for CD86 staining.

Gamma Counterscreen: Stimulation of Human Monocytes for Phospho-AKT Expression

A human monocyte cell line, THP-1, was maintained in RPMI+10% FBS (Gibco). One day before stimulation, cells were counted using trypan blue exclusion on a hemocytometer and suspended at a concentration of $1\times10^6$ cells per mL of media. 100 µL of cells plus media ($1\times10^5$ cells) was then aliquoted per well of 4-96-well, deep well dishes (Nunc) to test eight different compounds. Cells were rested overnight before treatment with various concentrations (from 10-0.0003 µM) of blocking compound. The compound diluted in media (12 mL) was added to the cells for 10 min at 37° C. Human MCP-1 (12 mL, R&D Diagnostics, #279-MC) was diluted in media and added to each well at a final concentration of 50 ng/mL. Stimulation lasted for 2 min at rt. Pre-warmed FACS Phosflow Lyse/Fix buffer (1 mL of 37° C.) (BD Biosciences, #558049) was added to each well. Plates were then incubated at 37° C. for an additional 10-15 min. Plates were spun at 1500 rpm for 10 min, supernatant was aspirated off, and 1 mL of ice cold 90% MeOH was added to each well with vigorous shaking. Plates were then incubated either overnight at −70° C. or on ice for 30 min before antibody staining. Plates were spun and washed 2× in PBS+2% FBS (Gibco). Wash was aspirated and cells were suspended in remaining buffer. Rabbit pAKT (50 µL, Cell Signaling, #4058L) at 1:100, was added to each sample for 1 h at rt with shaking. Cells were washed and spun at 1500 rpm for 10 min. Supernatant was aspirated and cells were suspended in remaining buffer. Secondary antibody, goat anti-rabbit Alexa 647 (50 mL, Invitrogen, #A21245) at 1:500, was added for 30 min at rt with shaking. Cells were then washed 1× in buffer and suspended in 150 µL of buffer for FACS analysis. Cells need to be dispersed very well by pipetting before running on flow cytometer. Cells were run on an LSR II (Becton Dickinson) and gated on forward and side scatter to determine expression levels of pAKT in the monocyte population.

Gamma Counterscreen Stimulation of Monocytes for Phospho-AKT Expression in Mouse Bone Marrow Mouse femurs were dissected from five female BALB/c mice (Charles River Labs.) and collected into RPMI+10% FBS media (Gibco). Mouse bone marrow was removed by cutting the ends of the femur and by flushing with 1 mL of media using a 25 gauge needle. Bone marrow was then dispersed in media using a 21 gauge needle. Media volume was increased to 20 mL and cells were counted using trypan blue exclusion on a hemocytometer. The cell suspension was then increased to $7.5\times10^6$ cells per 1 mL of media and 100 µL ($7.5\times10^5$ cells) was aliquoted per well into 4-96-well, deep well dishes (Nunc) to test eight different compounds. Cells were rested at 37° C. for 2 h before treatment with various concentrations (from 10-0.0003nM) of blocking compound. Compound diluted in media (12 mL) was added to bone marrow cells for 10 min at 37° C. Mouse MCP-1 (12 mL, R&D Diagnostics, #479-JE) was diluted in media and added to each well at a final concentration of 50 ng/mL. Stimulation lasted for 2 min at rt. 1 mL of 37° C. pre-warmed FACS Phosflow Lyse/Fix buffer (BD Biosciences, #558049) was added to each well. Plates were then incubated at 37° C. for an additional 10-15 min. Plates were spun at 1500 rpm for 10 min. Supernatant was aspirated off and 1 mL of ice cold 90% MeOH was added to each well with vigorous shaking. Plates were then incubated either overnight at −70° C. or on ice for 30 min before antibody staining. Plates were spun and washed 2× in PBS+2% FBS (Gibco). Wash was aspirated and cells were suspended in remaining buffer. Fc block (2 mL, BD Pharmingen, #553140) was then added per well for 10 min at rt. After block, 50 µL of primary antibodies diluted in buffer; CD11b-Alexa488 (BD Biosciences, #557672) at 1:50, CD64-PE (BD Biosciences, #558455) at 1:50, and rabbit pAKT (Cell Signaling, #4058L) at 1:100, were added to each sample for 1 h at RT with shaking. Wash buffer was added to cells and spun at 1500 rpm for 10 min. Supernatant was aspirated and cells were suspended in remaining buffer. Secondary antibody; goat anti-rabbit Alexa 647 (50 mL, Invitrogen, #A21245) at 1:500, was added for 30 min at rt with shaking. Cells were then washed 1× in buffer and suspended in 100 µL of buffer for FACS analysis. Cells were run on an LSR II (Becton Dickinson) and gated on CD11b/CD64 double positive cells to determine expression levels of pAKT in the monocyte population.

pAKT In Vivo Assay

Vehicle and compounds are administered p.o. (0.2 mL) by gavage (Oral Gavage Needles Popper & Sons, New Hyde Park, N.Y.) to mice (Transgenic Line 3751, female, 10-12 wks Amgen Inc, Thousand Oaks, Calif.) 15 min prior to the injection i.v (0.2 mLs) of anti-IgM FITC (50 ug/mouse) (Jackson Immuno Research, West Grove, Pa.). After 45 min the mice are sacrificed within a $CO_2$ chamber. Blood is drawn via cardiac puncture (0.3 mL) (1cc 25 g Syringes, Sherwood, St. Louis, Mo.) and transferred into a 15 mL conical vial (Nalge/Nunc International, Denmark). Blood is immediately fixed with 6.0 mL of BD Phosflow Lyse/Fix Buffer (BD Bioscience, San Jose, Calif.), inverted 3X's and placed in 37° C. water bath. Half of the spleen is removed and transferred to an eppendorf tube containing 0.5 mL of PBS (Invitrogen Corp, Grand Island, N.Y.). The spleen is crushed using a tissue grinder (Pellet Pestle, Kimble/Kontes, Vineland, N.J.) and immediately fixed with 6.0 mL of BD Phosflow Lyse/Fix buffer, inverted 3X's and placed in 37° C. water bath. Once tissues have been collected the mouse is cervically-dislocated and carcass to disposed. After 15 min, the 15 mL conical vials are removed from the 37° C. water bath and placed on ice until tissues are further processed. Crushed spleens are filtered through a 70 µm cell strainer (BD Bioscience, Bedford, Mass.) into another 15 mL conical vial and washed with 9 mL of PBS. Splenocytes and blood are spun @ 2,000 rpms for 10 min (cold) and buffer is aspirated. Cells are resuspended in 2.0 mL of cold (−20° C.) 90% methyl alcohol (Mallinckrodt Chemicals, Phillipsburg, N.J.). MeOH is slowly added while conical vial is rapidly vortexed. Tissues are then stored at −20° C. until cells can be stained for FACS analysis.

Multi-Dose TNP Immunization

Blood was collected by retro-orbital eye bleeds from 7-8 week old BALB/c female mice (Charles River Labs.) at day 0 before immunization. Blood was allowed to clot for 30 min and spun at 10,000 rpm in serum microtainer tubes (Becton Dickinson) for 10 min. Sera were collected, aliquoted in Matrix tubes (Matrix Tech. Corp.) and stored at −70° C. until ELISA was performed. Mice were given compound orally before immunization and at subsequent time periods based on the life of the molecule. Mice were then immunized with either 50 ng of TNP-LPS (Biosearch Tech., #T-5065), 50 ng of TNP-Ficoll (Biosearch Tech., #F-1300), or 100 ng of TNP-KLH (Biosearch Tech., #T-5060) plus 1% alum (Brenntag, #3501) in PBS. TNP-KLH plus alum solution was prepared by gently inverting the mixture 3-5 times every 10 min for 1 h before immunization. On day 5, post-last treatment, mice were $CO_2$ sacrificed and cardiac punctured. Blood was allowed to clot for 30 min and spun at 10,000 rpm in serum microtainer tubes for 10 min. Sera were collected, aliquoted in Matrix tubes, and stored at −70° C. until further analysis was performed. TNP-specific IgG1, IgG2a, IgG3 and IgM levels in the sera were then measured via ELISA. TNP-BSA (Biosearch Tech., #T-5050) was used to capture the TNP-specific antibodies. TNP-BSA (10 ng/mL) was used to coat 384-well ELISA plates (Corning Costar) overnight. Plates were then washed and blocked for 1 h using 10% BSA ELISA Block solution (KPL). After blocking, ELISA plates were washed and sera samples/standards were serially diluted and allowed to bind to the plates for 1 h. Plates were washed and Ig-HRP conjugated secondary antibodies (goat anti-mouse IgG1, Southern Biotech #1070-05, goat anti-mouse IgG2a, Southern Biotech #1080-05, goat anti-mouse IgM, Southern Biotech #1020-05, goat anti-mouse IgG3, Southern Biotech #1100-05) were diluted at 1:5000 and incubated on the plates for 1 h. TMB peroxidase solution (SureBlue Reserve TMB from KPL) was used to visualize the antibodies. Plates were washed and samples were allowed to develop in the TMB solution approximately 5-20 min depending on the Ig analyzed. The reaction was stopped with 2M sulfuric acid and plates were read at an OD of 450 nm.

| Ex # | PI3K d IC50 (µM) | PI3K b IC50 (µM) | PI3Ka IC50 (µM) | PI3Kg IC50 (µM) | PI3K: b/d | PI3K: a/d | PI3K: g/d |
|---|---|---|---|---|---|---|---|
| 1 | 0.0030 | 4.7400 | 9.9800 | 1.6100 | 1580 | 3327 | 537 |
| 2 | 0.0078 | 1.3600 | 7.0400 | 0.8040 | 174 | 903 | 103 |
| 3 | 0.0051 | 0.4340 | 3.4200 | 0.0629 | 85 | 671 | 12 |
| 4 | 0.0100 | 0.5220 | 12.0600 | 0.4480 | 52 | 1206 | 45 |
| 5 | 0.0026 | 0.6520 | 5.1600 | 0.6200 | 251 | 1985 | 238 |
| 6 | 0.0070 | 5.8000 | 25.0000 | 2.8000 | 829 | 3571 | 400 |
| 7 | 0.0117 | 2.4900 | 12.7000 | 3.9000 | 213 | 1085 | 333 |

| Ex # | on target anti-IgM mu splenocytes pAKT (Hu splenocytes PAKT) | PI3KIII, (uM) | PI3KbMDA468 FH PI3KbMBMDA468 (uM) | in vivo pAKT data, $ED_{50}$ (uM) WB, spleenocytes |
|---|---|---|---|---|
| 1 | 0.0022 | >10 | 5.97, 2.6 | 0.041, 0.010 |
| 2 | 0.0012 | >10 | >10, 0.811 | 0.36, 0.26 |
| 3 | 0.0015 | >10 | 3.8000, 0.483 | no data |
| 4 | 0.0018 | >10 | 1.9500, 0.62 | no data |
| 5 | 0.0050 | >10 | >10, >10 | 0.056, 0.012 |
| 6 | 0.0060 | >10 | 10, 11 | 0.13 (WB) |
| 7 | 0.0104 (Hu B Cell anti-IgM) | >10 | >10 | no data |

For the treatment of PI3Kδ-mediated-diseases, such as rheumatoid arthritis, ankylosing spondylitis, osteoarthritis, psoriatic arthritis, psoriasis, inflammatory diseases, and autoimmune diseases, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, rheumatoid arthritis, ankylosing spondylitis, osteoarthritis, psoriatic arthritis, psoriasis, inflammatory diseases, and autoimmune diseases and the like.

The dosage regimen for treating PI3Kδ-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aq. or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, isopropoxymethyl, α-methoxyethyl, groups such as α-((C₁-C₄)-alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:

1. A method of treating a condition in a mammal in need thereof, selected from of rheumatoid arthritis, ankylosing spondylitis, osteoarthritis, psoriatic arthritis, psoriasis, inflammatory bowel disorders, inflammatory eye disorders, inflammatory or unstable bladder disorders, systemic lupus erythematosis (SLE), myestenia gravis, acute disseminated encephalomyelitis, idiopathic thrombocytopenic purpura, multiples sclerosis, Sjoegren's syndrome and autoimmune hemolytic anemia comprising the step of administering a therapeutically-effective amount of compound selected from:

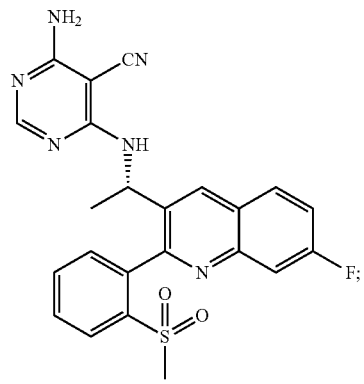 [SMILES: C[C@H](Nc1ncnc(N)c1C#N)c1cc2ccc(F)cc2nc1-c1ccccc1S(C)(=O)=O]

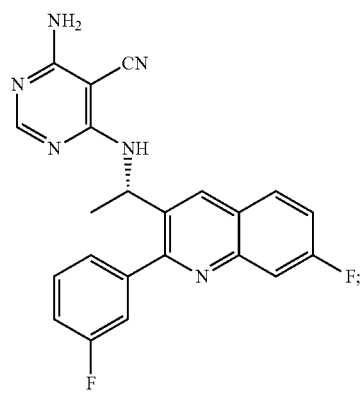 [SMILES: C[C@H](Nc1ncnc(N)c1C#N)c1cc2ccc(F)cc2nc1-c1cccc(F)c1]

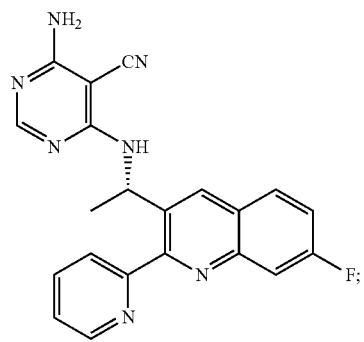 [SMILES: C[C@H](Nc1ncnc(N)c1C#N)c1cc2ccc(F)cc2nc1-c1ccccn1]

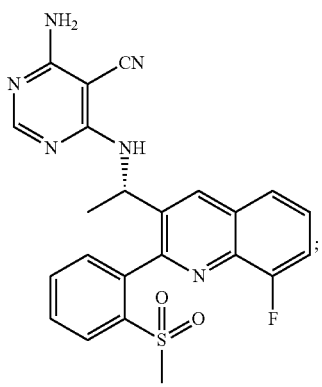

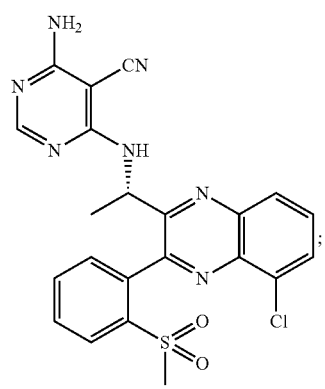 [SMILES: C[C@H](Nc1ncnc(N)c1C#N)c1nc2cccc(Cl)c2nc1-c1ccccc1S(C)(=O)=O]

[Structure: 4-amino-5-cyano-pyrimidine connected via NH-CH(CH3)- to quinoxaline bearing 2-(methylsulfonyl)phenyl and 8-cyano substituents]

and

[Structure: 4-amino-5-cyano-pyrimidine connected via NH-CH(CH3)- to quinoxaline bearing 2-pyridyl and 7-fluoro substituents]

or any pharmaceutically-acceptable salt thereof.

2. A method according to claim 1, wherein the compound is

[Structure: 4-amino-5-cyano-pyrimidine connected via NH-CH(CH3)- to quinoline bearing 2-(methylsulfonyl)phenyl and 8-fluoro substituents]

or any pharmaceutically-acceptable salt thereof.

3. A method according to claim 1, wherein the compound is

[Structure: 4-amino-5-cyano-pyrimidine connected via NH-CH(CH3)- to quinoline bearing 2-(methylsulfonyl)phenyl and 7-fluoro substituents]

or any pharmaceutically-acceptable salt thereof.

4. A method according to claim 1, wherein the compound is

[Structure: 4-amino-5-cyano-pyrimidine connected via NH-CH(CH3)- to quinoline bearing 2-(3-fluorophenyl) and 7-fluoro substituents]

or any pharmaceutically-acceptable salt thereof.

5. A method according to claim 1, wherein the compound is

[Structure: 4-amino-5-cyano-pyrimidine connected via NH-CH(CH3)- to quinoline bearing 2-pyridyl and 7-fluoro substituents]

or any pharmaceutically-acceptable salt thereof.

6. A method according to claim 1, wherein the compound is

[Structure: 4-amino-5-cyano-pyrimidine connected via NH-CH(CH3)- to quinoxaline bearing 2-(methylsulfonyl)phenyl and 8-chloro substituents]

or any pharmaceutically-acceptable salt thereof.

7. A method according to claim 1, wherein the compound is
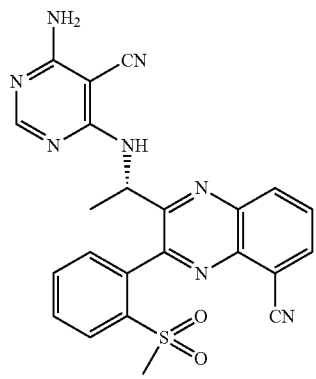 [SMILES: C[C@H](Nc1ncnc(N)c1C#N)c1nc2cccc(C#N)c2nc1-c1ccccc1S(C)(=O)=O]
or any pharmaceutically-acceptable salt thereof.
8. A method according to claim 1, wherein the compound is
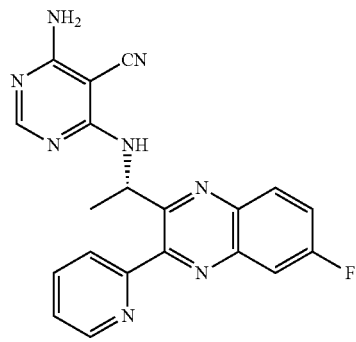 [SMILES: C[C@H](Nc1ncnc(N)c1C#N)c1nc2ccc(F)cc2nc1-c1ccccn1]
or any pharmaceutically-acceptable salt thereof.
* * * * *